United States Patent
Wood et al.

(10) Patent No.: US 7,790,754 B2
(45) Date of Patent: Sep. 7, 2010

(54) ALPHA-HYDROXY AMIDES AS BRADYKININ ANTAGONISTS OR INVERSE AGONISTS

(75) Inventors: Michael R. Wood, Harleysville, PA (US); Neville J. Anthony, Chalfont, PA (US); Mark G. Bock, Hatfield, PA (US); Scott D. Kuduk, Harleysville, PA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 1104 days.

(21) Appl. No.: 10/583,675

(22) PCT Filed: Dec. 17, 2004

(86) PCT No.: PCT/US2004/042691
§ 371 (c)(1), (2), (4) Date: Jun. 19, 2006

(87) PCT Pub. No.: WO2005/063690
PCT Pub. Date: Jul. 14, 2005

(65) Prior Publication Data
US 2008/0318976 A1  Dec. 25, 2008

Related U.S. Application Data

(60) Provisional application No. 60/531,643, filed on Dec. 22, 2003, provisional application No. 60/539,637, filed on Jan. 28, 2004, provisional application No. 60/624,658, filed on Nov. 4, 2004.

(51) Int. Cl.
A61K 31/4439 (2006.01)
C07D 413/10 (2006.01)

(52) U.S. Cl. .................. 514/338; 546/269.1
(58) Field of Classification Search .......... 546/269.1; 514/338
See application file for complete search history.

(56) References Cited

FOREIGN PATENT DOCUMENTS

WO  WO 02/076964 A1  10/2002
WO  WO 03/066577 A1  8/2003

OTHER PUBLICATIONS

Chemcial Abstracts, 1990, Abstract No. 112:55871 (for JP01157955, published Jun. 21, 1989).

Primary Examiner—Patricia L Morris
(74) Attorney, Agent, or Firm—Mollie M. Yang; Valerie J. Camara

(57) ABSTRACT

α-Hydroxy amide derivatives of the general formula (I) are bradykinin B1 antagonists or inverse agonists useful in the treatment or prevention of symptoms such as pain and inflammation associated with the bradykinin B1 pathway. $R^{2a}$ is selected from (1) a group selected from $R^a$. (2) $(CH_2)_n NR^b C(O)R^a$. (3) $(CH_2)_n NR^b SO_2 R^d$. (4) $(CH_2)_n NR^b CO_2 R^a$. (5) $(CH_2)_k$-heterocycle optionally substituted with 1 to 3 groups independently selected from halogen, nitro, cyano, $OR^a$, $SR^a$, $C_{1-4}$ alkyl and $C_{1-3}$ haloakyl wherein said heterocycle is (a) a 5-membered heteroaromatic ring having a ring heteroatom selected from N, O and S, and optionally having up to 3 additional ring nitrogen atoms wherein said ring is optionally benzo-fused; or (b) a 6-membered heteromatic ring containing from 1 to 3 ring nitrogen atoms and N-oxydes thereof. Wherein said ring is optionally benzo-fused. (6) $(CH_2)_k CO_2 R^a$. and (7) $(CH_2)_n C(O)NR^b R^c$. $R^{2b}$ is OH or a group selected from $R^{2a}$; or $R^{2a}$ and $R^{2b}$ together with the carbon atom to which they are attached form a 3- to 7-membered carbocyclic ring optionally substituted with 1 to 4 groups independently selected from halogen. $OR^a$. $C_{1-4}$ alkyl and $C_{1-4}$ haloalkyl.

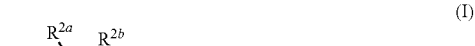

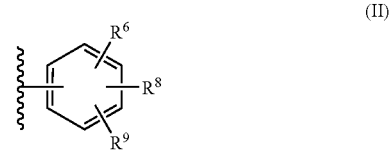

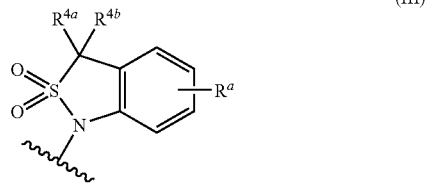

10 Claims, No Drawings

ALPHA-HYDROXY AMIDES AS BRADYKININ ANTAGONISTS OR INVERSE AGONISTS

CROSS REFERENCE TO RELATED APPLICATIONS

This application is the National Stage of International Application No. PCT/US2004/042691, filed 17 Dec. 2004 which claims the benefit under 35 U.S.C. 119(e) of U.S. Provisional Application No. 60/531,643 filed 22 Dec. 2003, U.S. Provisional Application No. 60/539,637 filed 28 Jan. 2004, and U.S. Provisional Application No. 60/624,958 filed 4 Nov. 2004.

BACKGROUND OF THE INVENTION

This invention is directed to α-hydroxyamide compounds. In particular, this invention is directed to α-hydroxyamide compounds that are bradykinin antagonists or inverse agonists.

Bradykinin ("BK") is a kinin which plays an important role in the pathophysiological processes accompanying acute and chronic pain and inflammation. Bradykinin (BK), like other kinins, is an autacoid peptide produced by the catalytic action of kallikrein enzymes on plasma and tissue precursors termed kininogens. The biological actions of BK are mediated by at least two major G-protein-coupled BK receptors termed B1 and B2. It is generally believed that B2 receptors, but not B1 receptors, are expressed in normal tissues and that inflammation, tissue damage or bacterial infection can rapidly induce B1 receptor expression. This makes the B1 receptor a particularly attractive drug target. The putative role of kinins, and specifically BK, in the management of pain and inflammation has provided the impetus for developing potent and selective BK antagonists. In recent years, this effort has been heightened with the expectation that useful therapeutic agents with analgesic and anti-inflammatory properties would provide relief from maladies mediated through a BK receptor pathway (see e.g., M. G. Bock and J. Longmore, *Current Opinion in Chem. Biol.*, 4:401-406 (2000)). Accordingly, there is a need for novel compounds that are effective in blocking or reversing activation of bradykinin receptors. Such compounds would be useful in the management of pain and inflammation, as well as in the treatment or prevention of diseases and disorders mediated by bradykinin; further, such compounds are also useful as research tools (in vivo and in vitro).

SUMMARY OF THE INVENTION

The present invention provides α-hydroxy amide derivatives which are bradykinin antagonists or inverse agonists, pharmaceutical compositions containing such compounds, and methods of using them as therapeutic agents.

DETAILED DESCRIPTION OF THE INVENTION

The present invention provides compounds of formula (I) and pharmaceutically acceptable salts thereof

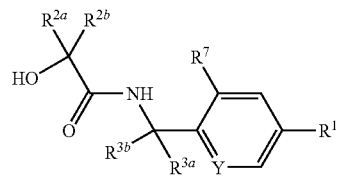

wherein

Y is CH or N;

$R^1$ is

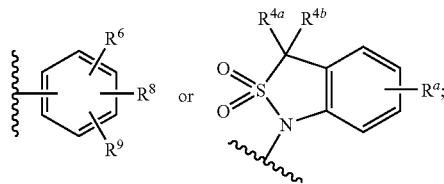

$R^{2a}$ is selected from (1) a group selected from $R^a$, (2) $(CH_2)_n NR^b C(O)R^a$, (3) $(CH_2)_n NR^b SO_2 R^d$, (4) $(CH_2)_n NR^b CO_2 R^a$, (5) $(CH_2)_k$-heterocycle optionally substituted with 1 to 3 groups independently selected from halogen, nitro, cyano, $OR^a$, $SR^a$, $C_{1-4}$ alkyl and $C_{1-3}$ haloalkyl wherein said heterocycle is (a) a 5-membered heteroaromatic ring having a ring heteroatom selected from N, O and S, and optionally having up to 3 additional ring nitrogen atoms wherein said ring is optionally benzo-fused; or (b) a 6-membered heteroaromatic ring containing from 1 to 3 ring nitrogen atoms and N-oxides thereof, wherein said ring is optionally benzo-fused, (6) $(CH_2)_k CO_2 R^a$, and (7) $(CH_2)_k C(O)NR^b R^c$, $R^{2b}$ is OH or a group selected from $R^{2a}$; or $R^{2a}$ and $R^{2b}$ together with the carbon atom to which they are attached form a 3- to 7-membered carbocyclic ring optionally substituted with 1 to 4 groups independently selected from halogen, $OR^a$, $C_{1-4}$ alkyl and $C_{1-4}$ haloalkyl;

$R^{3a}$ and $R^{3b}$ are independently selected from hydrogen, $C_{1-4}$ alkyl, and $C_{1-4}$ haloalkyl;

$R^{4a}$ and $R^{4b}$ are independently selected from hydrogen and halogen;

$R^6$ is selected from (1) $C_{1-8}$ alkyl optionally substituted with 1-5 groups independently selected from halogen, nitro, cyano, $COR^a$, $CO_2R^a$, $C(O)NR^bR^c$, $OR^a$, $OC(O)R^a$, $SR^a$, $SO_2R^d$, $S(O)R^d$, $NR^bR^c$, $NR^bC(O)R^a$, $NR^bSO_2R^d$, and $NR^bCO_2R^a$, (2) $C_{3-8}$ cycloalkyl, (3) $C_{2-8}$ alkenyl optionally substituted with $CO_2R^a$, (4) halogen, (5) cyano, (6) nitro, (7) $NR^bR^c$, (8) $NR^bC(O)R^a$, (9) $NR^bCO_2R^a$, (10) $NR^bC(O)NR^b R^c$, (11) $NR^bC(O)NR^bCO_2R^a$, (12) $NR^bSO_2R^d$, (13) $CO_2R^a$, (14) $COR^a$, (15) $C(O)NR^bR^c$, (16) $C(O)NHOR^a$, (17) $C(=NOR^a)R^a$, (18) $C(=NOR^a)NR^bR^c$, (19) $OR^a$, (20) $OC(O)R^a$, (21) $S(O)_xR^d$, (22) $SO_2NR^bR^c$, (23) optionally substituted heterocycle where the heterocycle is (a) a 5-membered heteroaromatic ring having a ring heteroatom selected from N, O and S, and optionally having up to 3 additional ring nitrogen atoms, (b) a 6-membered heteroaromatic ring having 1 to 3 ring N atoms, (c) 4,5-dihydro-oxazolyl or (d) 4,5-dihydro-1,2,4-oxadiazolyl, and wherein said substituent is 1 to 3 groups independently selected from $C_{1-4}$ alkyl optionally substituted with 1 to 5 halogen atoms, $OR^a$ or $OC(O)R^a$, (24) phenyl optionally substituted with 1 to 3 groups independently selected from halogen, nitro, cyano, $OR^a$, $SR^a$, $C_{1-4}$ alkyl and $C_{1-4}$ haloalkyl, and (25) $OSO_2R^d$;

$R^7$ is selected from hydrogen and halogen;

$R^8$ and $R^9$ are independently selected from hydrogen and a group from $R^6$; with the proviso that not more than one of $R^6$, $R^8$, and $R^9$ is a heterocycle;

$R^a$ is selected from (1) hydrogen, (2) $C_{1-7}$ alkyl optionally substituted with 1 to 5 halogen atoms, OH, SH, O—$C_{1-4}$alkyl, or S—$C_{1-4}$alkyl, (3) $(CH_2)_k$-phenyl optionally substituted with 1 to 3 groups independently selected from halogen, cyano, nitro, OH, $C_{1-4}$alkyloxy, $C_{3-6}$ cycloalkyl, $C_{1-4}$ alkyl and $C_{1-4}$haloalkyl, and (4) $C_{3-6}$ cycloalkyl;

$R^b$ and $R^c$ are independently selected from (1) hydrogen, (2) $C_{1-4}$ alkyl optionally substituted with 1 to 5 groups independently selected from halogen, amino, $CO_2R^a$, $OR^a$, mono-$C_{1-4}$ alkylamino, and di-$C_{1-4}$alkylamino, (3) $(CH_2)_k$-phenyl optionally substituted with 1 to 3 groups selected from halogen, cyano, nitro, $OR^a$, $CO_2R^a$, $C_{3-6}$ cycloalkyl, $C_{1-4}$ alkyl and $C_{1-4}$haloalkyl, and (4) $C_{3-6}$ cycloalkyl, or $R^b$ and $R^c$ together with the nitrogen atom to which they are attached form a 4-, 5-, or 6-membered ring optionally containing an additional heteroatom selected from $NR^e$, O, S, S(O) and $S(O)_2$;

$R^d$ is selected from (1) $C_{1-4}$ alkyl, (2) $C_{1-4}$haloalkyl, (3) $C_{1-4}$ alkyloxy, (4) $(CH_2)_k$-phenyl optionally substituted with 1 to 3 groups selected from halogen, cyano, nitro, $OR^a$, $CO_2R^a$, $C_{3-6}$ cycloalkyl, $C_{1-4}$ alkyl and $C_{1-4}$haloalkyl, (5) pyridyl, and (6) pyridyl N-oxide;

$R^e$ is selected from hydrogen, $C_{1-4}$ alkyl, $C_{1-4}$ haloalkyl, $C(O)H$ and $C(O)C_{1-4}$alkyl;

n is 1, 2, or 3;

k is 0, 1, 2, 3, or 4; and v is 0, 1, or 2.

Examples of $R^{2a}$ and $R^{2b}$ include, without limitation, hydrogen, methyl, ethyl, n-propyl, isopropyl, n-butyl, sec-butyl, isobutyl, t-butyl, n-pentyl, neo-pentyl, n-hexyl, n-heptyl, trifluoromethyl, 2,2,2-trifluoroethyl, 1,1-difluoroethyl, cyclopropyl, cyclobutyl, cyclopentyl, cyclohexyl, cycloheptyl, phenyl, benzyl, o-, m- or p-tolyl, xylyl, (trifluoromethyl) phenyl, cyanophenyl, bromophenyl, chloro-phenyl, dichlorophenyl, fluorophenyl, difluorophenyl, hydroxyphenyl, dihydroxyphenyl, methoxyphenyl, dimethoxyphenyl, (hydroxy)(methoxy)phenyl, 3-indolylmethyl, pyrrolyl, thiazolyl, oxazolyl, imidazolyl, 2-benzothienyl, isoxazolyl, isothiazolyl, quinolinyl, 2-(acethylamino)ethyl, (methylsulfonylamino)-methyl, carboxy, carbamoylmethyl, and 2-(methoxycarbonylamino)ethyl. $R^{2a}$, $R^{2b}$ and the carbon to which they are attached together may form cyclopropyl, cyclobutyl, cyclopentyl, cyclohexyl or cycloheptyl, each of which may be optionally substituted with 1 to 4 groups selected from, for example, methyl, ethyl, n-propyl, isopropyl, n-butyl, sec-butyl, isobutyl, t-butyl, chlorine, fluorine, bromine, chloromethyl, trifluoromethyl, 1-chloroethyl, hydroxy, methoxy, and ethoxy.

Examples of $R^{3a}$ and $R^{3b}$ include, without limitation, hydrogen, methyl, ethyl, n-propyl, isopropyl, n-butyl, sec-butyl, isobutyl, t-butyl, chloromethyl, fluoromethyl, difluoromethyl, trifluoro-methyl, 2,2,2-trifluoroethyl, 2,2-difluoroethyl, 1,1,2,2,2-pentafluoroethyl, and the like.

Examples of $R^6$ include methyl, ethyl, 1-methylethyl, 1-hydroxyethyl, carboxy, methoxy-carbonyl, ethoxycarbonyl, 2-fluoroethoxycarbonyl, isopropoxycarbonyl, phenoxycarbonyl, cyclopentoxy-carbonyl, cyclobutoxycarbonyl, cyclopropoxycarbonyl, 2,2,2-trifluoroethoxycarbonyl, 4-trifluoromethyl-phenoxycarbonyl, methoxyaminocarbonyl, methoxycarbonylmethyl, formyl, hydroxy, 5-methyl-1,2,4-oxadiazol-3-yl, 3-methyl-1,2,4-oxadiazol-5-yl, 1-methyl-5-tetrazolyl, 2-methyl-5-tetrazolyl, cyano, methoxy, ethoxy, difluoromethoxy, trifluoromethoxy, 2,2-difluoroethoxy, 1,3-difluoropropoxy, 2,2,2-trifluoroethoxy, trifluoromethyl, chloro, fluoro, methylaminosulfonyl, dimethylaminosulfonyl, methoxy-carbonylamino, ethoxycarbonylamino, 2-fluoroethoxycarbonylamino, methylaminocarbonylamino, dimethylamino, methylaminocarbonyl, isopropylaminocarbonyl, ethylaminocarbonyl, cyclopropylamino-carbonyl, cyclobutylaminocarbonyl, dimethylaminocarbonyl, and aminocarbonyl. Examples for $R^8$ include hydrogen, chloro, fluoro and methoxycarbonyl; examples of $R^9$ include hydrogen, chloro, fluoro and methyl.

In one subset of formula I are compounds wherein $R^{2a}$, $R^{2b}$ and the carbon atom to which they are attached form a 3- to 7-membered carbocyclic ring, said ring being optionally substituted with 1 to 4 groups independently selected from halogen, $OR^a$, $C_{1-4}$ alkyl and $C_{1-4}$ haloalkyl. In one embodiment the carbocyclic ring is substituted by methyl or halogen.

In a second subset of formula I are compounds wherein one of $R^{3a}$ and $R^{3b}$ is hydrogen and the other is hydrogen or methyl.

In a third subset of formula I are compounds wherein $R^1$ is

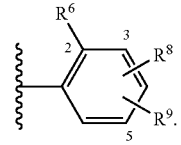

In one embodiment within this subset are compounds wherein $R^6$ is selected from (1) —$CO_2$—$C_{1-4}$alkyl, (2) $C_{1-4}$alkoxy, and (3) a 5-membered heteroaromatic ring having a ring heteroatom selected from N, O and S, and optionally having up to 3 additional ring nitrogen atoms, said ring being optionally substituted with a $C_{1-4}$alkyl group. In one embodiment $R^6$ is selected from methoxycarbonyl, ethoxy, 1,2,4-oxadiazolyl optionally substituted with a methyl group, and tetrazolyl optionally substituted with a methyl group. In another embodiment within this subset are compounds wherein $R^8$ is hydrogen or 3-halogen. In yet another embodiment within this subset are compounds wherein $R^8$ is hydrogen or 3-halogen, and $R^9$ is hydrogen or 5-halogen.

In a fourth subset of formula I are compounds of formula (Ia) and pharmaceutically acceptable salts thereof:

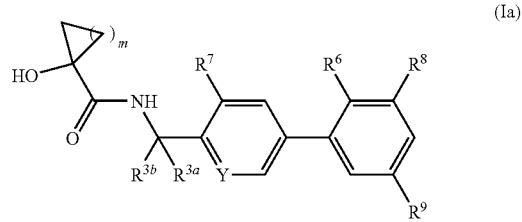

(Ia)

wherein m is 1 to 5; Y is N or CH; one of $R^{3a}$ and $R^{3b}$ is hydrogen and the other is hydrogen or methyl; $R^7$ is hydrogen or fluorine; $R^6$ is selected from (1) —$CO_2$—$C_{1-4}$alkyl, (2) $C_{1-4}$alkoxy optionally substituted with 1 to 5 halogen atoms, and (3) a 5-membered heteroaromatic ring having a ring heteroatom selected from N, O and S, and optionally having up to 3 additional ring nitrogen atoms, said ring being optionally substituted with a $C_{1-4}$alkyl group; and $R^8$ and $R^9$ are independently hydrogen or halogen.

In a fifth subset of compounds of formula I are compounds wherein $R^1$ is

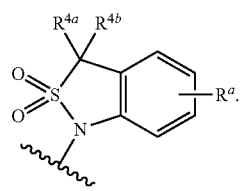

In one embodiment within this subset $R^a$ is H. In another embodiment, $R^{4a}$ and $R^{4b}$ are each a halogen exemplified by fluorine.

In a sixth subset of compounds of formula I are compounds of formula Ib and pharmaceutically acceptable salts thereof:

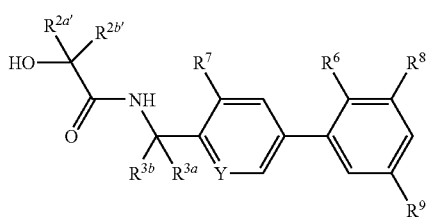

where $R^{3a}$, $R^{3b}$, $R^6$, $R^7$, $R^8$ and $R^9$ are as defined under formula I. $R^{2a'}$ and $R^{2b'}$ are independently selected from (1) hydrogen, (2) $C_{1-7}$ alkyl optionally substituted with 1 to 5 halogen atoms, SH, OH, S—$C_{1-4}$alkyl or $OC_{1-4}$alkyl, (3) $(CH_2)_k$-phenyl optionally substituted with 1 to 3 groups independently selected from halogen, cyano, nitro, OH, $C_{1-4}$ alkyloxy, $C_{3-6}$ cycloalkyl, $C_{1-4}$ alkyl and $C_{1-4}$haloalkyl, (4) $C_{3-6}$ cycloalkyl, (5) $(CH_2)_k$-pyridyl, and (6) $(CH_2)_k$-indolyl. In one embodiment within this subset are compounds wherein $R^{2a'}$ and $R^{2b'}$ are independently $C_{1-7}$alkyl optionally substituted with 1 to 5 halogen atoms. In another embodiment are compounds wherein one of $R^{3a}$ and $R^{3b}$ is hydrogen and the other is hydrogen or methyl; $R^7$ is hydrogen, chlorine or fluorine; $R^6$ is selected from (1) —$CO_2$—$C_{1-4}$alkyl, (2) $C_{1-4}$alkoxy optionally substituted with 1 to 5 halogen atoms, and (3) a 5-membered heteroaromatic ring having a ring heteroatom selected from N, O and S, and optionally having up to 3 additional ring nitrogen atoms, said ring being optionally substituted with a $C_{1-4}$alkyl group; and $R^8$ and $R^9$ are independently hydrogen or halogen.

In a seventh subset of compounds of formula I are compounds of formula Ic and pharmaceutically acceptable salts thereof:

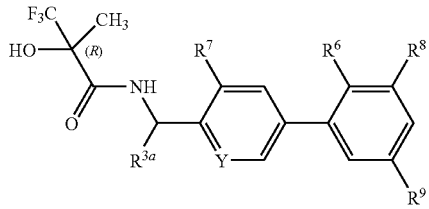

wherein Y is N or CH; $R^7$ is H, chlorine or fluoroine; $R^{3a}$ is H or methyl; $R^6$ is selected from (1) —$CO_2$—$C_{1-4}$alkyl, (2) $C_{1-4}$alkoxy, (3) $C_{1-4}$haloalkyloxy, and (4) a 5-membered heteroaromatic ring having a ring heteroatom selected from N, O and S, and optionally having up to 3 additional ring nitrogen atoms, said ring being optionally substituted with a $C_{1-4}$alkyl group; and $R^8$ and $R^9$ are independently hydrogen or halogen. In one embodiment, $R^8$ is fluorine or chlorine. In another embodiment $R^8$ and $R^9$ are each independently fluorine or chlorine. In yet another embodiment, $R^6$ is optionally methyl substituted tetrazolyl or optionally methyl substituted 1,2,4-oxadiazolyl. In another embodiment $R^7$ is chlorine or fluoroine, $R^6$ is optionally methyl substituted tetrazolyl or optionally methyl substituted 1,2,4-oxadiazolyl, $R^8$ is fluorine or chlorine, and $R^9$ is H, chlorine or fluorine.

A second aspect of the present invention provides a pharmaceutical composition comprising a therapeutically effective amount of a compound of formula (I) or a pharmaceutically acceptable salt thereof, and a pharmaceutically acceptable carrier.

A third aspect of the present invention provides the use of a compound of formula I or a pharmaceutically acceptable salt thereof for the manufacture of a medicament for the treatment of conditions mediated by bradykinin B1 receptor. In one subset said condition is pain including acute, inflammatory and neuropathic pain.

A fourth aspect of the present invention provides a method for the treatment of a condition mediated by bradykinin B1 receptor in a mammal comprising administering to said mammal a therapeutically effective amount of a compound of formula (I) or a pharmaceutically acceptable salt thereof.

Unless otherwise stated, the following terms have the meanings indicated below:

"Alkenyl" means carbon chains which may be linear or branched or combination thereof and containing at least one C=C bond. Examples of alkenyl include allyl, 2-butenyl, 3-butenyl, 1-methyl-2-propenyl, and the like.

"Alkyl" as well as other groups having the prefix "alk" such as, for example, alkoxy, alkanoyl, and the like, means carbon chains which may be linear or branched or combinations thereof. Examples of alkyl groups include methyl, ethyl, propyl, isopropyl, butyl, sec- and tert-butyl, pentyl, hexyl, heptyl and the like.

"Cycloalkyl" means carbocycles containing no heteroatoms, and includes mono-, bi- and tricyclic saturated carbocycles, as well as fused ring systems. Such fused ring systems can include one ring that is partially or fully unsaturated such as a benzene ring to form fused ring systems such as benzofused carbocycles. Cycloalkyl includes such fused ring systems as spirofused ring systems. Examples of cycloalkyl include cyclopropyl, cyclobutyl, cyclopentyl, cyclohexyl, decahydronaphthalene, adamantane, indanyl, indenyl, fluorenyl, 1,2,3,4-tetrahydronaphthalene and the like.

"Haloalkyl" means an alkyl radical as defined above wherein at least one and up to all of the hydrogen atoms are replaced with a halogen. Examples of such haloalkyl radicals include chloromethyl, 1-bromoethyl, fluoromethyl, difluoromethyl, trifluoromethyl, 2,2,2-trifluoroethyl and the like.

"Halogen" means fluorine, chlorine, bromine and iodine.

"5-Membered heteroaromatic ring" and "benzo-fused 5-membered heteroaromatic ring" include, without limitation, pyrrole, imidazole, pyrazole, 1,2,3-triazole, 1,2,4-triazole, tetrazole, furan, thiophene, thiazole, oxazole, isothiazole, isoxazole, 1,2,4-oxadiazole, 1,2,5-oxadiazole, 1,2,4-thiadiazole, 1,2,5-thiadiazole, benzofuran, benzothiophene, indole, benzimidazole, benzothiazole, benzoxazole, benzisothiazole, and benzisoxazole.

"6-Membered heteroaromatic ring" and "benzo-fused 6-membered heteroaromatic ring" include, without limitation, pyridine, pyrimidine, pyridazine, pyrazine, triazine, quinoline, isoquinoline and quinoxaline.

Optical Isomers—Diastereomers—Geometric Isomers—Tautomers.

Compounds described herein may contain an asymmetric center and may thus exist as enantiomers. Where the compounds according to the invention possess two or more asymmetric centers, they may additionally exist as diastereomers. The present invention includes all such possible stereoisomers as substantially pure resolved enantiomers, racemic mixtures thereof, as well as mixtures of diastereomers. The above Formula I is shown without a definitive stereochemistry at certain positions. The present invention includes all stereoisomers of Formula I and pharmaceutically acceptable salts thereof. Diastereoisomeric pairs of enantiomers may be separated by, for example, fractional crystallization from a suitable solvent, and the pair of enantiomers thus obtained may be separated into individual stereoisomers by conventional means, for example by the use of an optically active acid or base as a resolving agent or on a chiral HPLC column. Further, any enantiomer or diastereomer of a compound of the general Formula I may be obtained by stereospecific synthesis using optically pure starting materials or reagents of known configuration.

Some of the compounds described herein contain olefinic double bonds, and unless specified otherwise, are meant to include both E and Z geometric isomers.

Some of the compounds described herein may exist with different points of attachment of hydrogen, referred to as tautomers. Such an example may be a ketone and its enol form known as keto-enol tautomers. The individual tautomers as well as mixture thereof are encompassed with compounds of Formula I.

Salts.

The term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (ic and ous), ferric, ferrous, lithium, magnesium, manganese (ic and ous), potassium, sodium, zinc and the like salts. Preferred are the ammonium, calcium, magnesium, potassium and sodium salts. Salts prepared from pharmaceutically acceptable organic non-toxic bases include salts of primary, secondary, and tertiary amines derived from both naturally occurring and synthetic sources. Pharmaceutically acceptable organic non-toxic bases from which salts can be formed include, for example, arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, dicyclohexylamine, lysine, methylglucamine, morpholine, piperazine, piperidine, polyamine resins, procaine, purines, theobromine, triethylamine, trimethylamine, tripropylamine, tromethamine and the like.

When the compound of the present invention is basic, its corresponding salt can be conveniently prepared from pharmaceutically acceptable non-toxic inorganic and organic acids. Such acids include, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluene-sulfonic acid and the like. Preferred are citric, hydrobromic, hydrochloric, maleic, phosphoric, sulfuric, and tartaric acids.

Prodrugs.

The present invention includes within its scope prodrugs of the compounds of this invention. In general, such prodrugs will be functional derivatives of the compounds of this invention which are readily convertible in vivo into the required compound. Thus, in the methods of treatment of the present invention, the term "administering" shall encompass the treatment of the various conditions described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs," ed. H. Bundgaard, Elsevier, 1985. Metabolites of these compounds include active species produced upon introduction of compounds of this invention into the biological milieu.

Pharmaceutical Compositions.

Another aspect of the present invention provides pharmaceutical compositions which comprises a compound of Formula I, or a pharmaceutically acceptable salt thereof, and a pharmaceutically acceptable carrier. The term "composition", as in pharmaceutical composition, is intended to encompass a product comprising the active ingredient(s), and the inert ingredient(s) (pharmaceutically acceptable excipients) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of Formula I, additional active ingredient(s), and pharmaceutically acceptable excipients.

The pharmaceutical compositions of the present invention comprise a compound represented by Formula I (or pharmaceutically acceptable salts thereof) as an active ingredient, a pharmaceutically acceptable carrier and optionally other therapeutic ingredients or adjuvants. The compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions may be conveniently presented in unit dosage form and prepared by any of the methods well known in the art of pharmacy.

In practice, the compounds represented by Formula I, or pharmaceutically acceptable salts thereof, of this invention can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion or as a water-in-oil liquid emulsion. In addition to the common dosage forms set out above, the compound represented by Formula I, or pharmaceutically acceptable salts thereof, may also be administered by controlled release means and/or delivery devices. The compositions may be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

Thus, the pharmaceutical compositions of this invention may include a pharmaceutically acceptable carrier and a compound or a pharmaceutically acceptable salt of Formula I. The compounds of Formula I, or pharmaceutically acceptable salts thereof, can also be included in pharmaceutical compositions in combination with one or more other therapeutically active compounds.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media may be employed. For example, water, glycols, oils, alcohols, flavoring agents, preservatives, coloring agents and the like may be used to form oral liquid preparations such as suspensions, elixirs and solutions; while carriers such as starches, sugars, microcrystalline cellulose, diluents, granulating agents, lubricants, binders, disintegrating agents, and the like may be used to form oral solid preparations such as powders, capsules and tablets. Because of their ease of administration, tablets and capsules are the preferred oral dosage units whereby solid pharmaceutical carriers are employed. Optionally, tablets may be coated by standard aqueous or nonaqueous techniques A tablet containing the composition of this invention may be prepared by compression or molding, optionally with one or more accessory ingredients or adjuvants. Compressed tablets may be prepared by compressing, in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Each tablet preferably contains from about 0.1 mg to about 500 mg of the active ingredient and each cachet or capsule preferably containing from about 0.1 mg to about 500 mg of the active ingredient.

Pharmaceutical compositions of the present invention suitable for parenteral administration may be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, dusting powder, or the like. Further, the compositions can be in a form suitable for use in transdermal devices. These formulations may be prepared, utilizing a compound represented by Formula I of this invention, or pharmaceutically acceptable salts thereof, via conventional processing methods. As an example, a cream or ointment is prepared by mixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories may be conveniently formed by first admixing the composition with the softened or melted carrier(s) followed by chilling and shaping in moulds.

In addition to the aforementioned carrier ingredients, the pharmaceutical formulations described above may include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing a compound described by Formula I, or pharmaceutically acceptable salts thereof, may also be prepared in powder or liquid concentrate form.

The following are examples of representative pharmaceutical dosage forms for the compounds of Formula I:

| Inj. Suspension (I.M.) | mg/mL | Tablet | mg/tab. | Capsule | mg/cap. |
|---|---|---|---|---|---|
| Cmpd of Formula I | 10 | Cmpd of Formula I | 25 | Cmpd of Formula I | 25 |
| Methylcellulose | 5.0 | Microcryst. Cellulose | 415 | Lactose Powder | 573.5 |
| Tween 80 | 0.5 | Povidone | 14.0 | Magnesium Stearate | 1.5 |
| Benzyl alcohol | 9.0 | Pregelatinized Starch | 43.5 | | 600 |
| Benzalkonium chloride | 1.0 | Magnesium Stearate | 2.5 | | |
| Water for injection to a total volume of 1 mL | | | 500 | | |

Utilities.

Compounds of this invention are antagonists or inverse agonists of bradykinin receptor, in particular the bradykinin B1 receptor, and as such are useful in the treatment and prevention of diseases and conditions mediated through the bradykinin receptor pathway such as pain and inflammation. The compounds would be effective in the treatment or prevention of pain including, for example, visceral pain (such as pancreatitis, interstitial cystitis, renal colic, prostatitis, chronic pelvic pain), neuropathic pain (such as postherpetic neuralgia, acute zoster pain, nerve injury, the "dynias", e.g., vulvodynia, phantom limb pain, root avulsions, radiculopathy, painful traumatic mononeuropathy, painful entrapment neuropathy, carpal tunnel syndrome, ulnar neuropathy, tarsal tunnel syndrome, painful diabetic neuropathy, painful polyneuropathy, trigeminal neuralgia), central pain syndromes (potentially caused by virtually any lesion at any level of the nervous system including but not limited to stroke, multiple sclerosis, spinal cord injury), and postsurgical pain syndromes (eg, postmastectomy syndrome, postthoracotomy syndrome, stump pain)), bone and joint pain (osteoarthritis), spine pain (e.g., acute and chronic low back pain, neck pain, spinal stenosis), shoulder pain, repetitive motion pain, dental pain, sore throat, cancer pain, burn pain, myofascial pain (muscular injury, fibromyalgia), postoperative, perioperative pain and preemptive analgesia (including but not limited to general surgery, orthopedic, and gynecological), chronic pain, dysmenorrhea (primary and secondary), as well as pain associated with angina, and inflammatory pain of varied origins (e.g. osteoarthritis, rheumatoid arthritis, rheumatic disease, teno-synovitis and gout, ankylosing spondylitis, bursitis).

Further, the compounds of this invention can also be used to treat hyperreactive airways and to treat inflammatory events associated with airways disease e.g. asthma including allergic asthma (atopic or non-atopic) as well as exercise-induced bronchoconstriction, occupational asthma, viral- or bacterial exacerbation of asthma, other non-allergic asthmas and "wheezy-infant syndrome". Compounds of the present invention may also be used to treat chronic obstructive pulmonary disease including emphysema, adult respiratory distress syndrome, bronchitis, pneumonia, allergic rhinitis (seasonal and perennial), and vasomotor rhinitis. They may also be effective against pneumoconiosis, including aluminosis, anthracosis, asbestosis, chalicosis, ptilosis, siderosis, silicosis, tabacosis and byssinosis.

Compounds of the present invention may also be used for the treatment of inflammatory bowel disease including Crohn's disease and ulcerative colitis, irritable bowel syndrome, pancreatitis, nephritis, cystitis (interstitial cystitis), uveitis, inflammatory skin disorders such as psoriasis and eczema, rheumatoid arthritis and edema resulting from trauma associated with burns, sprains or fracture, cerebral edema and angioedema (including hereditary angioedema and drug-induced angioedema such as that caused by angiotensin converting enzyme (ACE) or ACE/neutral endopeptidase inhibitors, e.g. omepatrilat). They may be used to treat diabetic vasculopathy, diabetic neuropathy, diabetic retinopathy, post capillary resistance or diabetic symptoms associated with insulitis (e.g. hyperglycemia, diuresis, proteinuria and increased nitrite and kallikrein urinary excretion). They may be used as smooth muscle relaxants for the treatment of spasm of the gastrointestinal tract or uterus. Additionally, they may be effective against liver disease, multiple sclerosis, cardiovascular disease, e.g. atherosclerosis, congestive heart failure, myocardial infarct; neurodegenerative diseases, eg. Parkinson's and Alzheimers disease, epilepsy, septic shock e.g. as anti-hypovolemic and/or anti-hypotensive agents, headache including cluster headache, migraine including prophylactic and acute use, stroke, closed head trauma, cancer, sepsis, gingivitis, osteoporosis, benign prostatic hyperplasia and hyperactive bladder. Animal models of these diseases and conditions are generally well known in the art, and may be suitable for evaluating compounds of the present invention for their potential utilities. Finally, compounds of the present invention are also useful as research tools (in vivo and in vitro).

The compounds of this invention are useful in the treatment of pain and inflammation by the administration of a tablet, cachet, or capsule each containing, for example, 0.1 mg, 0.5 mg, 1 mg, 3 mg, 5 mg, 10 mg, 25 mg, 50 mg, 10 mg, 125 mg, 250 mg, or 500 mg of a compound of this invention once every three to four hours, once, twice or three times a day, or (in an extended release formulation) once, twice or three times a week.

The compounds would be effective in the treatment or prevention of pain including, for example, bone and joint pain (osteoarthritis), repetitive motion pain, dental pain, cancer pain, myofascial pain (muscular injury, fibromyalgia), perioperative pain (general surgery, oral surgery, gynecological), neuropathic pain (post-herpetic neuralgia), and chronic pain by the administration of a tablet, cachet, or capsule each containing, for example, 0.1 mg, 0.5 mg, 1 mg, 3 mg, 5 mg, 10 mg, 25 mg, 50 mg, 100 mg, 125 mg, 250 mg, or 500 mg of a compound of this invention once every three to four hours, once, twice or three times a day, or (in an extended release formulation) once, twice or three times a week.

In particular, inflammatory pain such as, for example, inflammatory airways disease (chronic obstructive pulmonary disease) would be effectively treated by the compounds of this invention by the administration of a tablet, cachet, or capsule each containing, for example, 0.1 mg, 0.5 mg, 1 mg, 3 mg, 5 mg, 10 mg, 25 mg, 50 mg, 100 mg, 125 mg, 250 mg, or 500 mg of a compound of this invention once every three to four hours, once, twice or three times a day, or (in an extended release formulation) once, twice or three times a week.

Further, the compounds of this invention can additionally be used to treat asthma, inflammatory bowel disease, rhinitis, pancreatitis, cystitis (interstitial cystitis), uveitis, inflammatory skin disorders, rheumatoid arthritis and edema resulting from trauma associated with burns, sprains or fracture by the administration of a tablet, cachet, or capsule each containing, for example, 0.1 mg, 0.5 mg, 1 mg, 3 mg, 5 mg, 10 mg, 25 mg, 50 mg, 100 mg, 125 mg, 250 mg, or 500 mg of a compound of this invention once every three to four hours, once, twice or three times a day, or (in an extended release formulation) once, twice or three times a week.

They may be used subsequent to surgical intervention (e.g. as post-operative analgesics) and to treat inflammatory pain of varied origins (e.g. osteoarthritis, rheumatoid arthritis, rheumatic disease, teno-synovitis and gout) as well as for the treatment of pain associated with angina, menstruation or cancer by the administration of a tablet, cachet, or capsule each containing, for example, 0.1 mg, 0.5 mg, 1 mg, 3 mg, 5 mg, 10 mg, 25 mg, 50 mg, 100 mg, 125 mg, 250 mg, or 500 mg of a compound of this invention once every three to four hours, once, twice or three times a day, or (in an extended release formulation) once, twice or three times a week.

They may be used to treat diabetic vasculopathy, post capillary resistance or diabetic symptoms associated with insulitis (e.g. hyperglycemia, diuresis, proteinuria and increased nitrite and kallikrein urinary excretion) by the administration of a tablet, cachet, or capsule each containing, for example, 0.1 mg, 0.5 mg, 1 mg, 3 mg, 5 mg, 10 mg, 25 mg, 50 mg, 100 mg, 125 mg, 250 mg, or 500 mg of a compound of this invention once every three to four hours, once, twice or three times a day, or (in an extended release formulation) once, twice or three times a week.

They may be used to treat inflammatory skin disorders such as psoriasis and eczema by the administration of a tablet, cachet, or capsule each containing, for example, 0.1 mg, 0.5 mg, 1 mg, 3 mg, 5 mg, 10 mg, 25 mg, 50 mg, 100 mg, 125 mg, 250 mg, or 500 mg of a compound of this invention once every three to four hours, once, twice or three times a day, or (in an extended release formulation) once, twice or three times a week.

They may be used as smooth muscle relaxants for the treatment of spasm of the gastrointestinal tract or uterus or in the therapy of Crohn's disease, ulcerative colitis or pancreatitis by the administration of a tablet, cachet, or capsule each containing, for example, 0.1 mg, 0.5 mg, 1 mg, 3 mg, 5 mg, 10 mg, 25 mg, 50 mg, 100 mg, 125 mg, 250 mg, or 500 mg of a compound of this invention once every three to four hours, once, twice or three times a day, or (in an extended release formulation) once, twice or three times a week.

Such compounds may be used therapeutically to treat hyperreactive airways and to treat inflammatory events associated with airways disease e.g. asthma, and to control, restrict or reverse airways hyperreactivity in asthma by the administration of a tablet, cachet, or capsule each containing, for example, 0.1 mg, 0.5 mg, 1 mg, 3 mg, 5 mg, 10 mg, 25 mg, 50 mg, 100 mg, 125 mg, 250 mg, or 500 mg of a compound of this invention once every three to four hours, once, twice or three times a day, or (in an extended release formulation) once, twice or three times a week.

They may be used to treat intrinsic and extrinsic asthma including allergic asthma (atopic or non-atopic) as well as exercise-induced bronchoconstriction, occupational asthma, viral or bacterial exacerbated asthma, other non-allergic asthmas and "wheezy-infant syndrome" by the administration of a tablet, cachet, or capsule each containing, for example, 0.1 mg, 0.5 mg, 1 mg, 3 mg, 5 mg, 10 mg, 25 mg, 50 mg, 100 mg, 125 mg, 250 mg, or 500 mg of a compound of this invention once every three to four hours, once, twice or three times a day, or (in an extended release formulation) once, twice or three times a week.

They may also be effective against pneumoconiosis, including aluminosis, anthracosis, asbestosis, chalicosis, ptilosis, siderosis, silicosis, tabacosis and byssinosis was well as adult respiratory distress syndrome, chronic obstructive pulmonary or airways disease, bronchitis, allergic rhinitis, and vasomotor rhinitis by the administration of a tablet, cachet, or capsule each containing, for example, 0.1 mg, 0.5 mg, 1 mg, 3 mg, 5 mg, 10 mg, 25 mg, 50 mg, 100 mg, 125 mg, 250 mg, or 500 mg of a compound of this invention once every three to four hours, once, twice or three times a day, or (in an extended release formulation) once, twice or three times a week.

Additionally, they may be effective against liver disease, multiple sclerosis, atherosclerosis, Alzheimer's disease, septic shock e.g. as anti-hypovolemic and/or anti-hypotensive agents, cerebral edema, headache including cluster headache, migraine including prophylactic and acute use, closed head trauma, irritable bowel syndrome and nephritis by the administration of a tablet, cachet, or capsule each containing, for example, 0.1 mg, 0.5 mg, 1 mg, 3 mg, 5 mg, 10 mg, 25 mg, 50 mg, 100 mg, 125 mg, 250 mg, or 500 mg of a compound of this invention once every three to four hours, once, twice or three times a day, or (in an extended release formulation) once, twice or three times a week.

Combination Therapy.

Compounds of Formula I may be used in combination with other drugs that are used in the treatment/prevention/suppression or amelioration of the diseases or conditions for which compounds of Formula I are useful. Such other drugs may be administered, by a route and in an amount commonly used therefor, contemporaneously or sequentially with a compound of Formula I. When a compound of Formula I is used contemporaneously with one or more other drugs, a pharmaceutical composition containing such other drugs in addition to the compound of Formula I is preferred. Accordingly, the pharmaceutical compositions of the present invention include those that also contain one or more other active ingredients, in addition to a compound of Formula I. Examples of other active ingredients that may be combined with a compound of Formula I, either administered separately or in the same pharmaceutical compositions, include, but are not limited to: (1) morphine and other opiate receptor agonists including codeine, oxycodone, propoxyphene (Darvon) and tramadol; (2) non-steroidal antiinflammatory drugs (NSAIDs) including COX-2 inhibitors such as propionic acid derivatives (alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac), fenamic acid derivatives (flufenamic acid, meclofenamic acid, mefenamic acid, niflumic acid and tolfenamic acid), biphenylcarboxylic acid derivatives (diflunisal and flufenisal), oxicams (isoxicam, piroxicam, sudoxicam and tenoxican), salicylates (acetyl salicylic acid, sulfasalazine) and the pyrazolones (apazone, bezpiperylon, feprazone, mofebutazone, oxyphenbutazone, phenylbutazone), and the coxibs (celecoxib, valecoxib, rofecoxib and etoricoxib); (3) corticosteroids such as betamethasone, budesonide, cortisone, dexamethasone, hydrocortisone, methylprednisolone, prednisolone, prednisone and triamcinolone; (4) histamine H1 receptor antagonists such as brompheniramine, chlorpheniramine, dexchlorpheniramine, triprolidine, clemastine, diphenhydramine, diphenylpyraline, tripelennamine, hydroxyzine, methdilazine, promethazine, trimeprazine, azatadine, cyproheptadine, antazoline, pheniramine pyrilamine, astemizole, terfenadine, loratadine, cetirizine, desloratadine, fexofenadine and levocetirizine; (5) histamine H2 receptor antagonists such as cimetidine, famotidine and ranitidine; (6) proton pump inhibitors such as omeprazole, pantoprazole and esomeprazole; (7) leukotriene antagonists and 5-lipoxygenase inhibitors such as zafirlukast, montelukast, pranlukast and zileuton; (8) drugs used for angina, myocardial ischemia including nitrates such as nitroglycerin and isosorbide nitrates, beta blockers such as atenolol, metoprolol, propranolol, acebutolol, betaxolol, bisoprolol, carteolol, labetalol, nadolol, oxprenolol, penbutolol, pindolol, sotalol and timolol, and calcium channel blockers such as diltiazam, verapamil, nifedipine, bepridil, felodipine, flunarizine, isradipine, nicardipine and nimodipine; (9) incontinence medications such as antimuscarinics, e.g., tolterodine and oxybutinin); (10) gastrointestinal antispasmodics (such as atropine, scopolamine, dicyclomine, antimuscarinics, as well as diphenoxylate); skeletal muscle relaxants (cyclobenzaprine, carisoprodol, chlorphenesin, chlorzoxazone, metaxalone, methocarbamol, baclofen, dantrolene, diazepam, or orphenadrine); (11) gout medications such as allopurinol, probenicid and colchicine; (12) drugs for rheumatoid arthritis such as methotrexate, auranofin, aurothioglucose and gold sodium thiomalate; (13) drugs for osteoporosis such as alendronate and raloxifene; (14) decongestants such as pseudoephedrine and phenylpropanolamine; (15) local anesthetics; (16) anti-herpes drugs such as acyclovir, valacyclovir and famciclovir; (17) antiemetics such as ondansetron and granisetron; (18) migraine drugs such as the triptans (e.g. rizatriptan, sumatriptan), ergotamine, dihydroergotamine, CGRP antagonists, (19) antidepressants (e.g., tricyclic antidepressants (such as doxepin, clomipramine, imipramine, amitriptyline, maprotiline, nortriptyline), serotonin-selective/serotonin and norepinephrine reuptake inhibitors (such as paroxetine, fluoxetine, duloxetine, vanlafexine), beta-adrenergic blockers; (20) VR1 antagonsits; (21) anticonvulsants (e.g., gabapentin, pregabalin, lamotrigine, topiramate, carbamazepine, oxcarbazepine, phenyloin); (22) glutamate antagonists (e.g., ketamine and other NMDA antagonists, NR2B antagonists); (23) acetaminophen; (24) CCR2 antagonists; (25) PDE4 antagonists such as roflumilast; (26) tegaserod; (27) alosetron; (28) topiramate; (29) cathepsin K inhibitors; and (30) ACE/NEP inhibitors such as omepatrilat.

Biological Evaluation.

(a) Assessing the Affinity of Selected Compounds to Bind to the Bradykinin B1 or B2 Receptor.

Radioligand binding assays are performed using membranes from CHO cells that stably express the human, rabbit, rat, or dog B1 receptors or CHO cells that express the human B2 receptor. For all receptor types, cells are harvested from culture flasks in PBS/1 mM EDTA and centrifuged at 1000×g for 10 minutes. The cell pellets are homogenized with a polytron in ice cold 20 mM HEPES, 1 mM EDTA, pH 7.4 (lysis buffer) and centrifuged at 20,000×g for 20 minutes. The membrane pellets are rehomogenized in lysis buffer, centrifuged again at 20,000×g and the final pellets are resuspended at 5 mg protein/ml in assay buffer (120 mM NaCl, 5 mM KCl, 20 nM HEPES, pH 7.4) supplemented with 1% BSA and frozen at −80° C.

On the day of assay, membranes are centrifuged at 14,000×g for 5 minutes and resuspended to the desired protein concentration in assay buffer containing 100 nM enaliprilat, 140 μg/mL bacitracin and 0.1% BSA. 3H-des-arg10, leu9 kallidin is the radioligand used for the human and rabbit B1 receptors, 3H-des-arg10 kallidin is used for the rat and dog B1 receptors, and 3H-bradykinin is used to label the human B2 receptor.

For all assays, compounds are diluted from DMSO stock solutions with 4 μL added to assay tubes for a final DMSO concentration of 2%. This is followed by the addition of 100 μL radioligand and 100 μL of the membrane suspension. Nonspecific binding for the B1 receptor binding assays is determined using 1 μM des-arg10 kallidin and nonspecific binding for the B2 receptor is determined with 1 μM bradykinin. Tubes are incubated at room temperature (22° C.) for 60 minutes followed by filtration using a Tomtec 96-well harvesting system. Radioactivity retained by the filter is counted using a Wallac Beta-plate scintillation counter.

The compounds of this invention have affinity for the B1 receptor in the above assay as demonstrated by results of less than 5 μM. It is advantageous that the assay results be less than 1 μM, even more advantageous for the results be less than 0.5 μM. It is further advantageous that compounds of this invention have affinity for the bradykinin B1 receptor over the bradykinin B2 receptor; more advantageously, the affinity for the B1 receptor is at least 10 fold, and preferably over 100 fold, over that for the B2 receptor.

(b) Assay for Bradykinin B1 Antagonists.

B1 agonist-induced calcium mobilization was monitored using a Fluorescence Imaging Plate Reader (FLIPR). CHO cells expressing the B1 receptor were plated in 96 or 384 well plates and allowed to incubate in Iscove's modified DMEM overnight. Wells were washed two times with a physiological buffered salt solution and then incubated with 4 uM Fluo-3 for one hour at 37° C. The plates were then washed two times with buffered salt solution and 100 uL of buffer was added to each well. Plates were placed in the FLIPR unit and allowed to equilibrate for two minutes. The test compound was then added in 50 ul volumes followed five minutes later by 50 ul of agonist (des-arg$^{10}$ kallidin). Relative fluorescence peak heights in the absence and presence of antagonist were used to calculate the degree of inhibition of the B1 receptor agonist response by the test compound. Eight to ten concentrations of test compound were typically evaluated to construct an inhibition curve and determine IC50 values using a four-parameter nonlinear regression curve fitting routine.

(c) Assay for Bradykinin Inverse Agonists.

Inverse agonist activity at the human B1 receptor was evaluated using transiently transfected HEK293 cells. One day following transfection cell flasks were labeled overnight with 6 uCi/ml [$^3$H]myo-inositol. On the day of assay, the media was removed and the attached cells were gently rinsed with 2×20 ml of phosphate-buffered saline. Assay buffer (HEPES buffered physiological salts, pH 7.4) was added and the cells were detached by tapping of the flask. The cells were centrifuged at 800×g for five minutes and resuspended at 1×10$^6$ cells/ml in assay buffer supplemented with 10 mM lithium chloride. After 10 minutes at room temperature, one-half mil aliquots were distributed to tubes containing test compound or vehicle. After an additional 10 minutes the tubes were transferred to a 37° C. water bath for 30 minutes. The incubation was terminated by the addition of a 12% perchloric acid solution and the tubes were placed on ice for 30 minutes. The acid was then neutralized with KOH and the tubes centrifuged to pellet precipitated material. [$^3$H]Inositol monophosphate formed was recovered by standard ion exchange chromatographic techniques and quantitated by liquid scintillation counting. Inverse agonist activity was determined by the degree to which a test compound reduced basal (cells incubated with vehicle) levels of [$^3$H]inositol monophosphate accumulation.

Abbreviations Used.

The following abbreviations have the meanings indicated, unless stated otherwise in the specification: Ac=acetyl; Boc=t-butoxycarbonyl; Cat.=catalyst; DCM=dichloromethane;

DMF=dimethylformamide; DMADMA=dimethylacetamide dimethyl acetal; DMSO=dimethyl sulfoxide;

EDCI=1-(3-dimethylaminopropyl)-3-ethylcarbodiimide; Et=ethyl; EtOAc=ethyl acetate; HOBT=1-hydroxybenzotriazole; LAH=lithium aluminum hydride; LDA=lithium diisopropylamide;

LiHMDS=lithium hexamethyldisilazide; Me=methyl; NBS=N-bromosuccinimide; Ph=phenyl; Rt=room temperature; Tf=triflyl (trifluoromethanesulfonyl); THF=tetrahydrofuran.

Methods of Synthesis.

Compounds of formula I may be prepared by the general procedure depicted in Scheme 1. The α-hydroxycarboxylic acid (1) is coupled with the arylmethylamine (2) using standard reagents and reaction conditions for amide bond formation, such as EDCI/HOBt.

matic halide (4) in the presence of a triarylphosphine, like triphenylphosphine, and a metal catalyst, like palladium acetate. The resultant cyano biphenyl intermediate (5), is then catalytically reduced to the biaryl amine derivative (2a) using hydrogen and a metal, like Raney Ni, in an appropriate solvent.

SCHEME 2

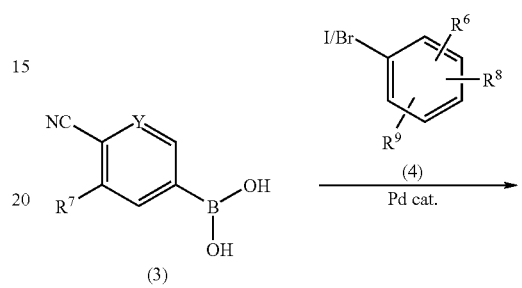

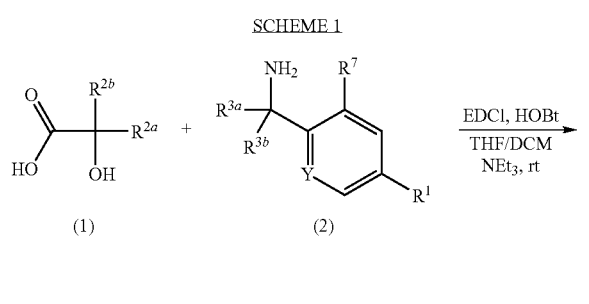

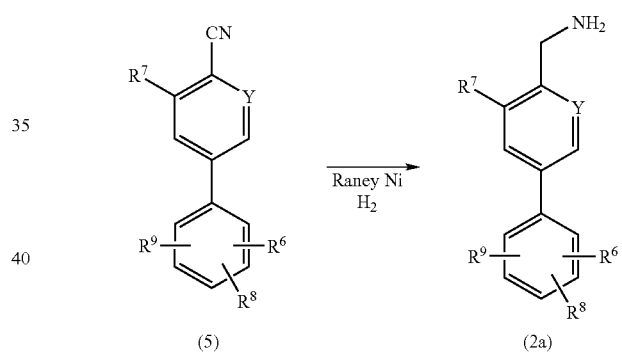

Alternatively, as illustrated in Scheme 3, the amine derivative (6), after primary amine protection with an appropriate protecting group, like Boc, is elaborated to the pinacol boron ester (8) using a palladium catalyst in an appropriate solvent, like dimethyl sulfoxide. This boron ester (8) is coupled to an aryl halide derivative (4) employing Suzuki reaction conditions to yield (2a) following deprotection.

SCHEME 3

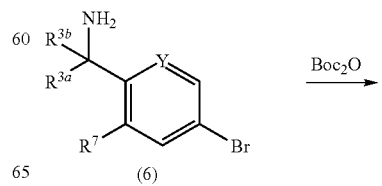

The carboxylic acids (1) are commercially available or may be prepared from commercially available reagents using conventional chemical reactions well known in the art. The amines (2) may be prepared as outlined in Schemes 2 to 6. In Scheme 2, the biaryl derivative (5) is assembled using a Suzuki reaction between an aromatic boronic acid derivative (3), or an appropriate boronic ester derivative, and an aro-

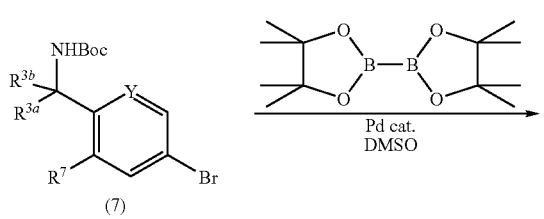

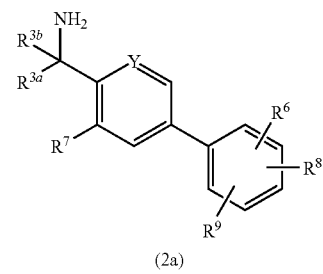

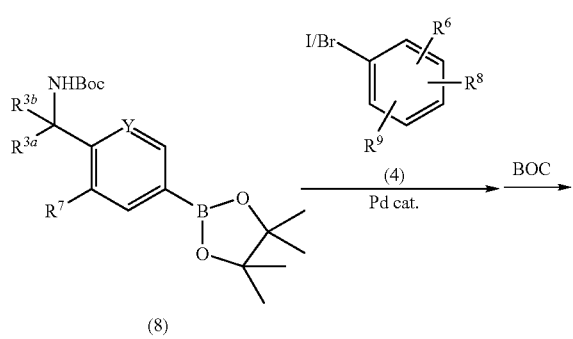

A third method for the preparation of biarylmethanamine derivatives is depicted in Scheme 4. The biaryl moiety (11) is first assembled using a palladium catalyzed coupling of (9) with an aryl zinc compound (10) as shown. The methyl group of biaryl (11) is then elaborated according to the three step sequence of halogenation, nucleophilic displacement of the halogen with azide, and reduction to provide the corresponding amine intermediate (2a). Alternatively, in a fourth method, the biarylmethanamine (2a) can also be prepared starting from the arylcarbonitrile (13) and aryl zinc compound (10) as previously discussed. The resulting biarylcarbonitrile (5) is then reduced using hydrogen to provide (2a).

SCHEME 4

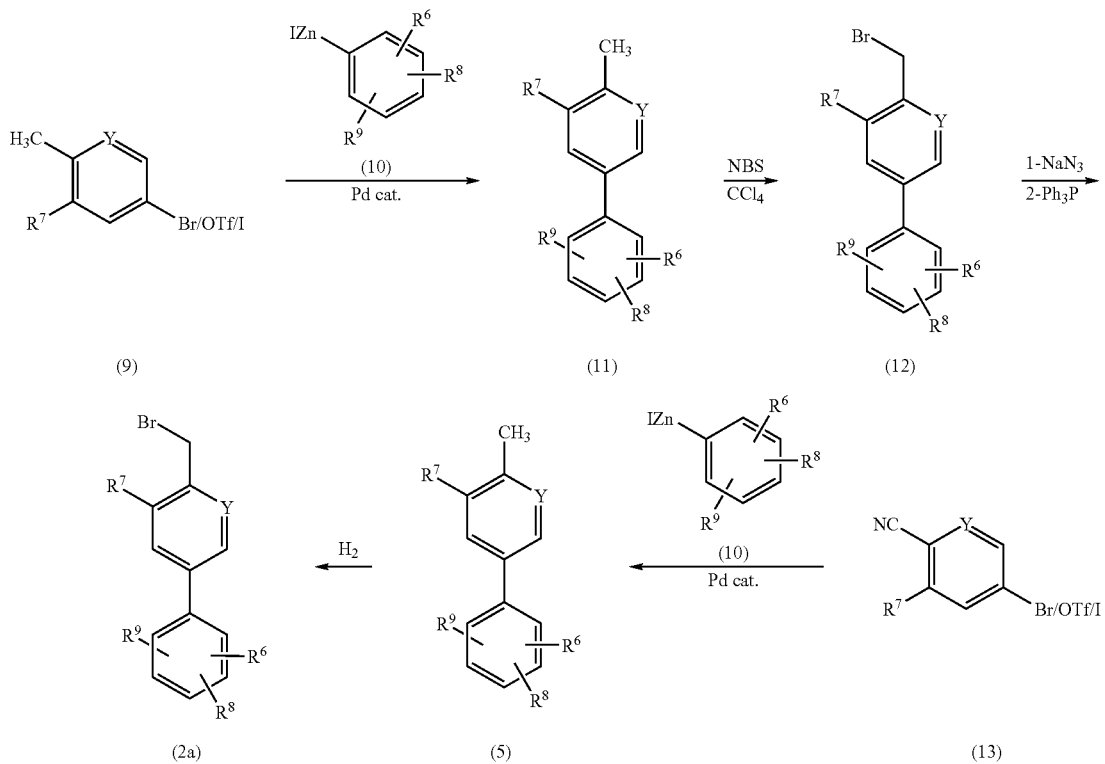

A fifth method for the preparation of biarylmethanamine derivatives is depicted in Scheme 5. Reduction of the nitro group and nitrile hydrolysis of known pyridine (14) (*J. Chem. Soc*, (1952), 2042-2046.) is followed by conversion of the resultant amine to the fluoride to afford (15). The amide is converted in a 3 step sequence to aldehyde (16). Imine formation with t-butyl sulfinamide is followed by addition of methyl Grignard to produce (17), which may be further elaborated to provide the biarylmethanamine as shown above.

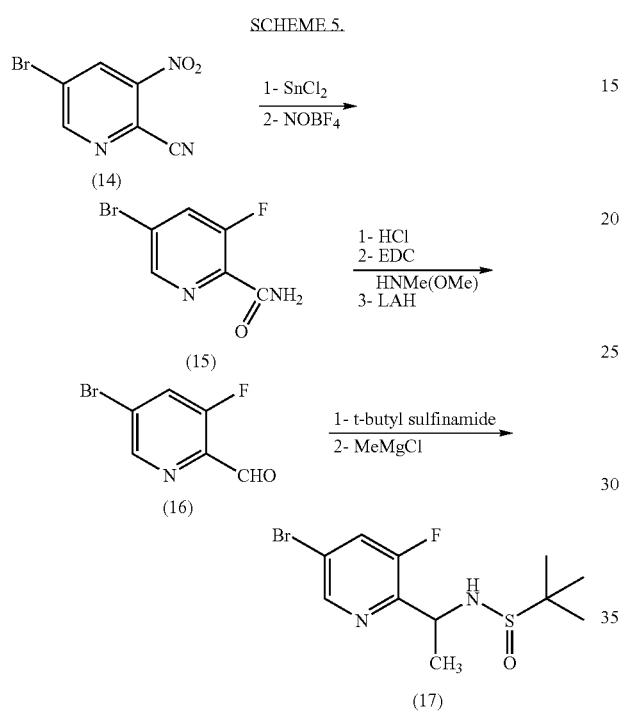

The reaction steps in Scheme 6 illustrates the preparation of a compound of Formula (I) wherein $R^1$ is the benzisothiazoline moiety. While Scheme 6 depicts the preparation of a specific compound, the procedure may be used to prepare other similar compounds of Formula (I).

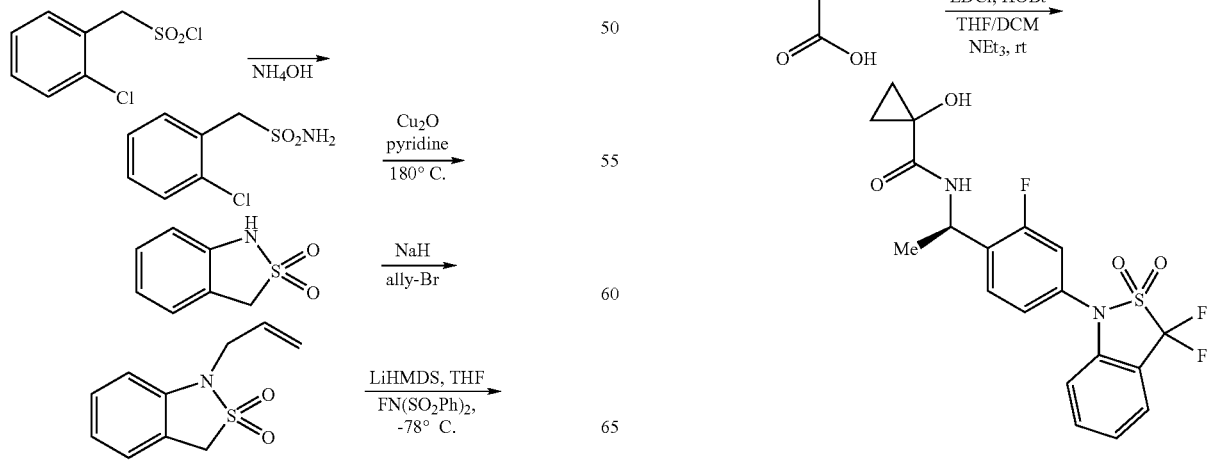

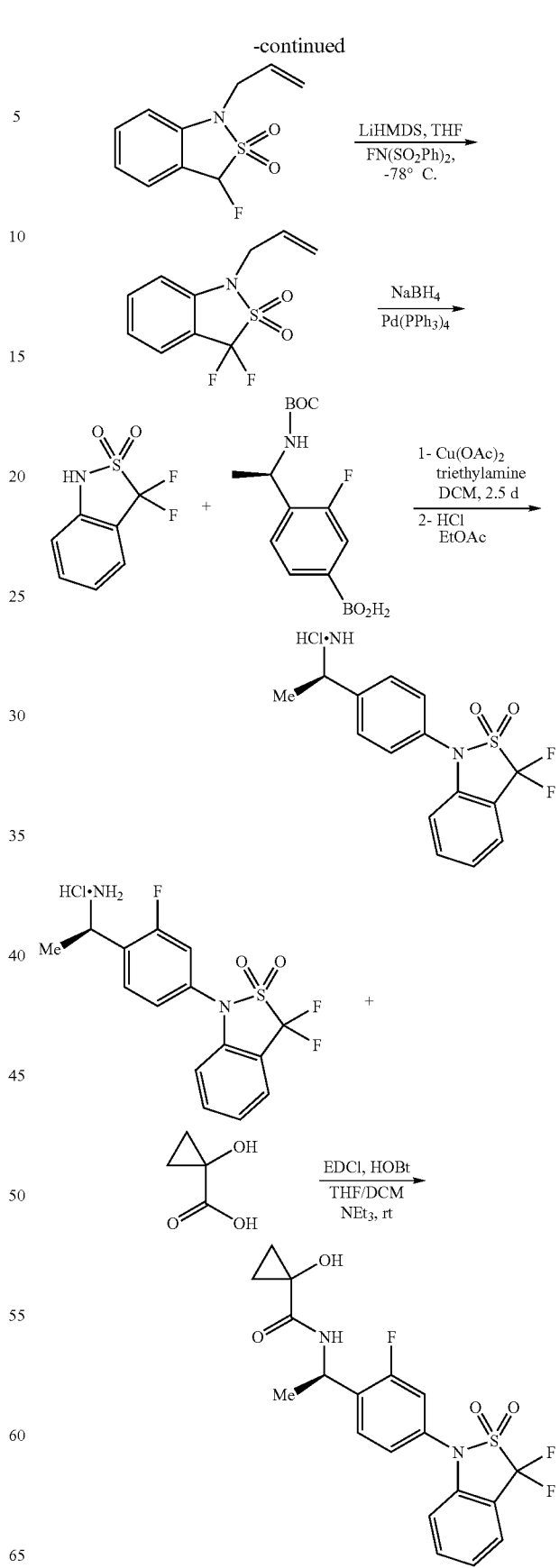

REFERENCE EXAMPLES

The following examples are provided to illustrate the preparation of the biarylmethylamine starting materials. Other biarylmethylamines may be similarly prepared.

I. Methyl 2-[6-(aminomethyl)-5-fluoropyridin-3-yl]-6-fluorobenzoate

A solution of LDA (40.9 μmmol, prepared from 11.4 mL of diisopropylamine and 16.4 mL of 2.5 M n-butyl lithium in hexanes) in 200 mL THF at −78° C. was treated with 2-cyano-3-fluoropyridine (5.0 g, 40.9 mmol) in 50 mL of THF drop-wise. After 10 minutes a solution of iodine (10.4 g, 40.9 mmol) in 10 mL of THF was added. After 30 minutes the reaction was quenched with 40 mL of water followed by workup with aqueous sodium thiosulfate. The mixture was diluted with ether, washed with brine, dried over $Na_2SO_4$, filtered and concentrated under vacuum. The residue was subjected to silica gel chromatography eluted with 0-20% ethyl acetate in hexanes to provide 3-fluoro-4-iodopyridine-2-carbonitrile that gave proton NMR spectra consistent with theory.

A solution of LDA (16.9 mmol) in 200 mL THF at −78° C. was treated with the above carbonitrile (4.2 g, 16.9 mmol) in 50 mL of THF drop-wise. After 2 hours the reaction was quenched with water and warmed to room temperature. The mixture was diluted with ether, washed with brine, dried over $Na_2SO_4$, filtered and concentrated under vacuum. The residue was subjected to silica gel chromatography eluted with 0-20% ethyl acetate in hexanes to provide 3-fluoro-5-iodopyridine-2-carbonitrile that gave proton NMR spectra consistent with theory.

A solution of the above carbonitrile (1.08 g, 3.87 mmol) in 10 mL of THF and palladium tetrakistriphenylphosphine (0.18 g, 0.16 mmol) was added to a solution of [3-fluoro-2-(methoxy-carbonyl)phenyl](iodo)zinc (prepared from methyl 2-fluoro-6-iodobenzoate and Reike Zinc) in 20 mL of THF via cannula. The mixture was heated to reflux for one hour, cooled, and partitioned between ethyl acetate and water. The organic extract was washed with brine, dried over $MgSO_4$, filtered and concentrated under vacuum. The residue was subjected to silica gel chromatography eluted with 0-20% ethyl acetate in hexanes to provide methyl 2-(6-cyano-5-fluoropyridin-3-yl)-6-fluorobenzoate that gave proton NMR spectra consistent with theory.

To a stirred solution of the above ester (0.75 g, 2.7 mmol) in $NH_3$/MeOH (5 mL, 2.0 M) was added Raney 2800 nickel (slurry in water). The mixture was stirred under a H2 atmosphere (balloon) at room temperature for 6 hours. The mixture was then filtered through glass filter paper, washing with additional MeOH. The resultant solution was concentrated under vacuum and azeotroped three times with toluene to provide crude title compound (0.65 g, 2.34 mmol).

II. (1R)-1-{5-[3,5-dichloro-2-(methoxycarbonyl) phenyl]-3-fluoropyridin-2-yl}ethanaminium chloride A solution of 2,4-dichloro-6-hydroxybenzaldehyde (5.00 g, 26.18 mmol) in 125 mL methanol was cooled to 0° C. Perchloric acid (70%, 1.47 mL, 16.23 mmol) was added, and the solution was stirred for 10 minutes. To a separate flask, vanadium (V) oxide (0.190 g, 1.05 mmol) was added to a hydrogen peroxide solution (30% in $H_2O$, 11.90 mL, 104.7 mmol) at 0° C. This solution was stirred until the catalyst was dissolved, resulting in a clear orange solution, which was added dropwise to the methanol solution. The reaction was allowed to slowly warm to room temperature and stir overnight. The solution was concentrated under vacuum, and the residue dissolved in ethyl acetate. The organic extract was washed with aqueous sodium bicarbonate and brine, dried over $Na_2SO_4$, filtered and concentrated. The residue was filtered through a silica gel plug with 10% ethyl acetate in hexanes to provide methyl 2,4-dichloro-6-hydroxybenzoate that gave proton NMR spectra consistent with theory.

A solution of the above ester (4.64 g, 20.99 mmol) and pyridine (1.87 mL, 23.09 mmol) in 100 mL $CH_2Cl_2$ was cooled to 0° C. Trifluoromethanesulfonic acid (4.94 mL, 29.39 mmol) was added, and the solution was stirred for 2 h. The reaction mixture was washed with aqueous sodium bicarbonate, aqueous copper sulfate and brine, dried over $Na_2SO_4$, filtered and concentrated to provide methyl 2,4-dichloro-6-{[(trifluoromethyl)sulfonyl]oxy}benzoate that gave proton NMR spectra consistent with theory.

To a solution of 5-bromo-3-nitropyridine-2-carbonitrile (4.71 g, 20.7 mmol) in MeOH (319 mL) under $N_2$ was added tin(II) chloride dihydrate (27.97 g, 123.9 mmol). The reaction was heated to 40° C. for 40 minutes, concentrated in vacuo, and azeotroped with toluene. The residue was dissolved in ethyl acetate, and 10% aqueous sodium bicarbonate was added till the solution was basic. The aqueous layer was extracted 3× with $CHCl_3$ and the combined organics were dried over $Na_2SO_4$, filtered and concentrated under vacuum to provide 3-amino-5-bromopyridine-2-carboxamide that gave a mass ion (ES+) of 218.2 for $M+H^{+(81Br)}$.

To a solution of the above carboxamide (40.0 g, 185.2 mmol) in $CH_2Cl_2$ was added nitrosonium tetrafluoroborate (22.7 μg, 191.4 mmol). The reaction was stirred at room temperature for 4.5 hours, then concentrated in vacuo and azeotroped with toluene. The residue was suspended in toluene (1100 mL) and heated to 100° C. for 2 hours. The reaction was concentrated in vacuo, and the residue suspended in $CH_2Cl_2$. The solid was collected to provide 5-bromo-3-fluoropyridine-2-carboxamide that gave proton NMR spectra consistent with theory and a mass ion (ES+) of 219.1 for $M+H^{+(79Br)}$.

A solution of the above crude carboxamide (40.50 g, 184.9 mmol) in HCl (12N, 539.4 mL, 6.472 mol) was heated to 120° C. for 1 hour. The reaction was cooled to room temperature, and NaOH (20%) was added slowly to pH ~6. The solution was concentrated in vacuo, and azeotroped 3× with toluene. The residue was extracted thoroughly with 40% MeOH/$CHCl_3$ and filtered. This was repeated three times. The combined filtrates were concentrated and azeotroped 3× with toluene to provide 5-bromo-3-fluoropyridine-2-carboxylic acid that gave a mass ion (ES+) of 218.1 for $M+H^{+(79Br)}$.

A solution of the above crude arboxylic acid (40.65 g, 184.8 mmol), O,N-dimethylhydroxyl-amine hydrochloride (21.63 g, 221.7 mmol), 1-ethyl-(3-dimethylaminopropyl)-carbodiimide hydrochloride (70.85 g, 369.6 mmol), 1-hydroxy-7-azabenzotriazole (2.497 g, 18.48 mmol), and triethylamine (16.48 mL, 118.3 mmol) in 200 mL DMF was stirred at RT overnight. The solution was partially concentrated in vacuo and partitioned between ethyl acetate and 10% aqueous sodium bicarbonate. The aqueous layer was extracted 4× with ethyl acetate, and the combined organics were washed with water and brine, dried over $Na_2SO_4$, filtered and concentrated under vacuum to provide 5-bromo-3-fluoro-N-methoxy-N-methylpyridine-2-carboxamide that gave proton NMR spectra consistent with theory and a mass ion (ES+) of 263.01 for $M+H^{+(79Br)}$.

To a solution of the above crude carboxamide (27.94 g, 106.2 mmol) in THF (350 mL) at −78° C. was added LAH (1M in THF, 45.67 mL, 45.67 mmol) dropwise. The reaction was stirred at –78° C. for 2 hours, then H$_2$O (100 mL) and brine (100 mL) were added. The mixture was warmed to RT and partially concentrated in vacuo, diluted with ethyl acetate and filtered through celite. The aqueous layer was extracted 4× with ethyl acetate. The combined organics were washed with brine, dried over Na$_2$SO$_4$, filtered and concentrated under vacuum. The residue was filtered through a silica gel plug with 10% ethyl acetate in hexanes to provide 5-bromo-3-fluoropyridine-2-carbaldehyde that gave proton NMR spectra consistent with theory.

To a solution of (R)-(+)-2-methyl-2-propanesulfinamide (9.898 g, 81.67 mmol) in CH$_2$Cl$_2$ (160 mL) was added 5-bromo-3-fluoropyridine-2-carbaldehyde (16.66 g, 81.67 mmol), pyridinium p-toluenesulfonate (1.026 g, 4.08 mmol), and magnesium sulfate (49.15 g, 408.3 mmol). The reaction was stirred at room temperature overnight, then filtered through celite and concentrated in vacuo. The residue was subjected to silica gel chromatography eluted with 0 to 10% ethyl acetate in hexanes to provide N-[(1E)-(5-bromo-3-fluoropyridin-2-yl)methylidene]-2-methylpropane-2-sulfinamide that gave proton NMR spectra consistent with theory and a mass ion (ES+) of 307.0 for M+H$^{+(81Br)}$.

A solution of the above sulfinamide (18.63 g, 60.65 mmol) in CH$_2$Cl$_2$ (375 mL) was cooled to –50° C. under N$_2$. Methylmagnesium chloride (3M in THF, 30.32 mL, 90.97 mmol) was added dropwise, the reaction was stirred for 1 h. Additional methylmagnesium chloride (5.0 mL, 15.0 mmol) was added after 30 minutes to drive the reaction to completion. Water (200 mL) and brine (200 mL) were added, and the reaction allowed to warm to room temperature. The aqueous layer was extracted 4× with CH$_2$Cl$_2$, and the combined organics were dried over Na$_2$SO$_4$, filtered and concentrated under vacuum. The residue was subjected to silica gel chromatography eluted with 10-40% ethyl acetate in hexanes to provide N-[(1R)-1-(5-bromo-3-fluoropyridin-2-yl)ethyl]-2-methylpropane-2-sulfinamide that gave proton NMR spectra consistent with theory and a mass ion (ES+) of 325.0 for M+H$^+$ (81Br).

A mixture of the above sulfinamide (0.500 g, 1.55 mmol), bis(pinacolato)diboron (0.412 g, 1.62 mmol), potassium acetate (0.456 g, 4.64 mmol), and [1,1'-bis(diphenylphosphino)ferrocene]-palladium(II) dichloride (0.030 g, 0.041 mmol) in 5 mL DMF was heated to 90° C. under N$_2$ for 4 hours. Additional bis(pinacolato)diboron (0.295 g, 1.16 mmol) and 3-chloroperoxybenzoic acid (861 mg, 4.99 mmol) and [1,1'-bis(diphenylphosphino)ferrocene]palladium(II) dichloride (0.030 g, 0.041 mmol) were added to drive the reaction to completion. The reaction mixture was cooled to room temperature, and methyl 2,4-dichloro-6-{[(trifluoromethyl)sulfonyl]oxy}benzoate (0.546 g, 1.55 mmol), sodium carbonate (2M, 2.32 mL, 4.64 mmol), and [1,1'-bis(diphenylphosphino)ferrocene]palladium(II) dichloride (0.003 g, 0.041 mmol) were added. The reaction mixture was heated to 90° C. 1.5 hours, then cooled to room temperature and partitioned between ethyl acetate and water. The organic extract was washed with water and brine, dried over Na$_2$SO$_4$, filtered and concentrated under vacuum. The residue was subjected to silica gel chromatography eluted with 0-30% ethyl acetate in hexanes to provide methyl 2-(6-{(1R)-1-[(tert-butylsulfinyl)amino]ethyl}-5-fluoropyridin-3-yl)-4,6-dichlorobenzoate that gave proton NMR spectra consistent with theory.

To a solution of the above product in methanol (1.2 mL) was added HCl/dioxane solution (4M, 1.2 mL, 4.6 mmol). The solution was stirred at room temperature 30 minutes, then concentrated in vacuo to provide the title compound (ES+) of 343.01 for M+H$^+$.

III. Methyl 4'-[(1R)-1-aminoethyl]-3-fluoro-1,1'-biphenyl-2-carboxylate HCl

Commercially available (1R)-1-(4-bromophenyl)ethanamine was Boc protected, using standard procedures known to those skilled in the art, to produce tert-butyl (1R)-1-(4-bromophenyl)ethyl-carbamate.

To a solution of the above carbamate (7.6 g, 25.3 mmol) in DMSO (20 mL) was added bis(pinacolato)diboron (7.07 g, 27.9 mmol), dichloro[1,1'-bis(diphenylphosphino)ferrocene] palladium (II) dichloromethane adduct (2.06 g, 2.53 mmol), and potassium acetate (7.45 g, 76.0 mmol) at room temperature under N$_2$. The resulting mixture was heated at 80° C. for 1 hour. The reaction was quenched by addition of EtOAc and filtered through celite. The organic extract was washed with water three times, saturated NaCl, dried over MgSO$_4$, filtered and concentrated under vacuum. The residue was purified on silica gel eluted with 0-20% ethyl acetate in hexane to provide tert-butyl (1R)-1-[4-(4,4,5,5-tetramethyl-1,3,2-dioxaborolan-2-yl)phenyl]ethylcarbamate as a clear light yellow oil with a mass ion (ES+) of 333.

To a stirred solution of the above carbamate (1.0 g, 2.9 mmol) and methyl 2-fluoro-6-iodobenzoate (1.2 g, 4.32 mmol) in 25 mL of a 5:1 THF:water mixture was added potassium carbonate (1.2 g, 8.64 mmol), tri-o-tolylphosphine (350 mg, 1.15 mmol) and lastly palladium acetate (65 mg, 0.29 mmol). The reaction vessel was then sealed and placed into a 90° C. oil bath for overnight stirring and heating. After about 18 hours the reaction mixture was cooled to ambient temperature and then diluted with EtOAc. The organics were washed with brine (×4), dried over sodium sulfate, filtered, and concentrated under reduced pressure to give an oil. This oil was subject to silica gel chromatography eluting with 10-60% EtOAc in hexanes to provide methyl 4'-{(1R)-1-[(tert-butoxycarbonyl)amino]-ethyl}-3-fluoro-1,1'-biphenyl-2-carboxylate (205 mg, found to be pure by LC/MS and proton NMR.

The above carboxylate (205 mg, 0.60 mmol) dissolved in MeOH (15 mL) was cooled to 0° C. This homogenous solution was saturated with anhydrous HCl and allowed to sit for 20 minutes. Dry nitrogen was then bubbled through the solution for about 30 minutes. Solvent was then removed under reduced pressure to yield an oily residue. The oil was then dissolved in DCM and the solvent removed. This process was repeated until a solid amine hydrochloride was obtained.

IV. N-[(1R)-1-(5-Bromo-3-fluoropyridin-2-yl)ethyl] acetamide

Step 1. 2,5-Dibromo-3-nitropyridine

2-Hydroxy-3-nitro-5-bromopyridine (1 eq) was suspended in toluene (3 vol) and N,N-dimethylformamide (0.1 eq) was added. The mixture was protected from light. A solution of phosphorus oxybromide (1.2 eq) in toluene (2 vol) was added to the pyridine mixture over 1.5 h at about 90° C. and the reaction was aged for about 14 h at 90° C. The reaction mixture was cooled to room temperature and water (10 vol) and toluene (5 vol) were added. The layers were cut and the organic layer was washed with 1N NaOH (2×10 vol) and H$_2$O (5 vol). The batch was concentrated under reduced pressure to yield the desired product.

Step 2. 5-Bromo-3-nitropyridine-2-carbonitrile

The compound of Step 1 (1 eq) was suspended in propionitrile (3 vol). Copper cyanide (1.1 eq) was added and the mixture was heated to 90° C. and aged for about 17 h. The reaction mixture was cooled to room temperature and isopropyl acetate (12 vol) and saturated brine (8 vol) were added. The mixture was stirred for 15 min and the layers were cut. The top organic layer was washed with brine (4×6 vol). The batch concentrated under reduced pressure to yield the desired product.

Step 3. 5-Bromo-3-fluoropyridine-2-carbonitrile

Sulfuric acid (0.02 eq) was added to a solution of tetrabutylammonium fluoride (3 eq) in DMF (5 vol) and the mixture cooled to −40° C. A solution of the compound of Step 2 (1 eq) in DMF (2 vol) was added maintaining the temperature <−35° C. After about 20 minutes 2N HCl (3 vol) was added followed by 1N HCl (15 vol). The precipitated product was collected by filtration to give the desired product.

Step 4.
N-[1-(5-Bromo-3-fluoropyridin-2-yl)vinyl]acetamide

Compound of Step 3 (1 eq) was dissolved in toluene (10 vol). The batch was cooled to −10° C. and MeMgCl (1.5 eq) was added maintaining the temperature<0° C. The mixture was aged for 1 h and acetic anhydride was added over approximately 30 min maintaining the temperature<0° C. The reaction was aged for 18 h at −10° C. The mixture was quenched with half-saturated $NaHCO_3$ (6 vol) and aged at 20-25° C. for 30 min. The layers were separated and the organic layer was washed with water (5 vol), 10% aqueous $Na_2SO_4$ (2×5 vol) and water (2×5 vol). The batch was concentrated under vacuum to give the title compound.

Step 5. N-[(1R)-1-(5-Bromo-3-fluoropyridin-2-yl)ethyl]acetamide

In a nitrogen filled glovebox (<10 ppm $O_2$), (S,S,R,R)-Tangphos (1.05 equivalents relative to Rh) was combined with $(COD)_2RhBF_4$ and dissolved in methanol to make a solution that was 0.107M in Rh. The catalyst solution was aged for 1 h.

In an nitrogen filled glovebox the catalyst solution (((S,S,R,R)-(Tangphos)Rh(COD)$BF_4$, 0.00284 eq, S/C=352) was transferred to a stainless steel cylinder along with methanol rinse (1 volume). To a separate stainless steel cylinder an additional charge of methanol (1 volume) was added. These two cylinders were connected via a ball-valve. The enamide of Step 4 (54 wt % in MeOH) was drawn into a stirred autoclave via vacuum followed by a methanol (10 mL/g enamide) rinse. The solution was then degassed with nitrogen (3×). The stainless steel vessels containing the catalyst solution were connected to the autoclave via flexible tubing. The autoclave was placed under partial vacuum and the catalyst solution was drawn into the autoclave followed by the MeOH rinse. The solution was degassed with $H_2$ (100 psig) 3× and the final pressure adjusted to 20 psig. The reaction temperature was set to 25° C. and agitation initiated. The reaction pressure was increased to 98 psig after 20 minutes. The mixture was hydrogenated for an additional 4 h. Enantiomeric excess was 99.5%.

The batch was removed from the autoclave and concentrated under vacuum and solvent switched to isopropyl acetate (IPAc) to a final concentration of 10 mL/g. The IPAc solution was filtered through silica gel (300 wt %), and washed with 1 volume of IPAc. Darko KB-B (50 wt %) was added and the mixture aged for 16 h at 20-25° C. The batch was filtered through Solka Floc and the cake washed with IPAc (1.1 volumes). The batch was concentrated under vacuum to give the title compound.

V. 3-(2-bromo-4-chloro-6-fluorophenyl)-5-methyl-1,2,4-oxadiazole

A solution of 2-bromo-4-chloro-6-fluoroaniline (25.0 g, 111 mmol) in 200 mL of anhydrous DCM, in a 2 liter round-bottom flask equipped with a bubbler, was treated with nitrosonium tetrafluoroborate (14.3 g, 123 mmol), at ambient temperature. After 1 hour complete consumption of the aniline was observed. The reaction mixture was cooled to 0° C. prior to the addition of potassium cyanide (14.5 g, 223 mmol). With rapid stirring, an aqueous solution of cupric sulfate hexahydrate (55.6 g, 223 mmol in 125 mL of water) was slowly added producing a large volume of gas evolution. After stirring for 40 minutes, the ice bath was removed and the reaction was allowed to warm to ambient temperature. After 1 hour at ambient temperature, the reaction mixture was diluted with additional DCM and then slowly quenched by the addition of aqueous saturated sodium bicarbonate until additional gas evolution is no longer observed. The resulting heterogeneous mixture was then filtered through a large pad of celite, washing with DCM as needed. The organic filtrate was then washed twice with saturated brine prior to drying over sodium sulfate. Filtration and solvent removal provided material which was subjected to silica gel chromatography eluting with 0-25% DCM in heptane. Collection of product containing fractions and removal of solvent yielded 9.76 grams of 2-bromo-4-chloro-6-fluorobenzo-nitrile, which gave LC/MS and proton NMR spectra consistent with theory.

To 21 mL of ethanol was added the above nitrile (5.00 g, 21.3 mmol) followed by excess hydroxylamine (21 mL of a 50% aqueous hydroxylamine solution). This mixture was then headed to 60° C. while open to the atmosphere. After 1.5 hours the reaction was judged complete by LC/MS analysis. The mixture was allowed to cool to ambient temperature before being diluted with diethyl ether and water. The ethereal layer was washed with additional water, then twice with saturated brine. The organic layer was dried over sodium sulfate, filtered and then concentrated to obtain 5.5 g of unpurified hydroxylamine adduct. This material was combined with an equivalent quantity of unpurified hydroxyl-amine adduct prepared in parallel to give a total mass of ~11.1 grams. This 11.1 grams of material was dissolved in DMADMA (38.7 g, 290. mmol) and allowed to stir at ambient temperature for 30 minutes. The reaction mixture was then diluted with diethyl ether and washed with water, half-saturated brine and then brine prior to drying over sodium sulfate. Filtration and solvent removal provided material which was subjected to silica gel chromatography eluting with 40-85% DCM in hexanes. Collection of product containing fractions and removal of solvent yielded 5.08 grams of the title compound, which gave LC/MS and proton NMR spectra consistent with theory.

The following examples are provided to illustrate the invention are not to be construed as limiting the scope of the claims in any manner.

Example 1

Methyl 4'-({[(1-hydroxycyclopropyl)carbonyl]amino}methyl)biphenyl-2-carboxylate

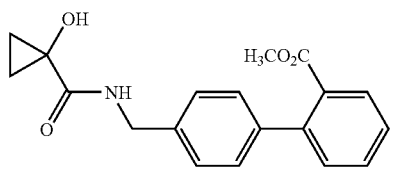

Methyl 4'-(aminomethyl)biphenyl-2-carboxylate (0.325 g, 1.35 mmol), 1-hydroxycyclo-propanecarboxylic acid (0.151 g, 1.48 mmol) and 1-hydroxybenzotriazole hydrate (0.248 g, 1.62 mmol) were suspended in a mixture of THF/DCM (13 mL of THF/6.5 mL of DCM), followed by the addition of 1-(3-dimethylaminopropyl)-3-ethylcarbodiimide hydrochloride (0.336 g, 1.75 mmol). Rapidly the solution turned homogenous, but returned to a heterogeneous mixture after 5 minutes. After 3 hours the solvent mixture was exchanged for pure DCM, prior to purification by silica gel chromatography eluted with 1-5% methanol in DCM to provide the title compound.

LRMS (ES, M+H$^+$): 326. $^1$H NMR (400 MHz, CDCl$_3$): δ 7.84 (dd, J=8.0, 1.2 Hz, 1H), 7.53 (td, J=7.6, 1.6 Hz, 1H), 7.41 (td, J=7.6, 1.2 Hz, 1H), 7.34 (m, 3H), 7.29 (bd, J=8.4 Hz, 2H), 7.19 (bs, 1H), 4.55 (d, J=6.0 Hz, 2H), 3.69 (s, 3H), 2.55 (bs, 1H), 1.43 (m, 2H), 1.07 (m, 2H).

Example 2

(2R)—N-((1R)-1-{5-[5-chloro-3-fluoro-2-(5-methyl-1,2,4-oxadiazol-3-yl)phenyl]-3-fluoropyridin-2-yl}ethyl)-3,3,3-trifluoro-2-hydroxy-2-methylpropanamide

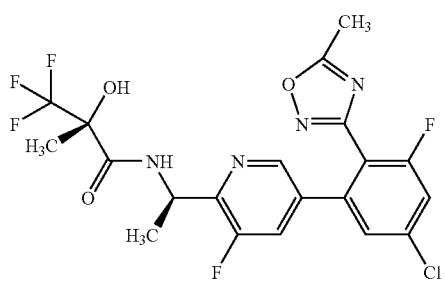

A solution of the compound of Reference Example IV (20.6 g, 79.1 mmol) in 210 mL of anhydrous MeOH was cooled to 0° C. prior to saturation with anhydrous hydrogen chloride. A condenser and oil bubbler were then attached, and the solution was heated to 85° C. for 5 hours. After cooling to ambient temperature, solvent was removed under reduced pressure to obtain a yellow solid. This solid was dissolved in 200 mL of DCM and 210 mL of aqueous sodium hydroxide (1M, 210 mmol). Boc-anhydride (23 g, 105 mmol) was then added and the reaction was allowed to stir for 16 hours. The layers were then separated and the organic layer was extracted once with DCM. The combined organics were washed with saturated brine prior to drying over sodium sulfate. Filtration and solvent removal provided material which was subjected to silica gel chromatography eluting with 5-30% EtOAc in hexanes. Collection of product containing fractions and removal of solvent yielded 25.1 grams of tert-butyl [(1R)-1-(5-bromo-3-fluoropyridin-2-yl)ethyl]carbamate, which gave LC/MS and proton NMR spectra consistent with theory.

A mixture of potassium acetate (3.43 g, 35.0 mmol), the above carbamate (3.72 g, 11.7 mmol) and 4,4,4',4',5,5,5',5'-octamethyl-2,2'-bi-1,3,2-dioxaborolane (3.85 g, 15.2 mmol) in a sealed tube reaction vessel caped with a rubber septum was dissolved in 24 mL of DMSO. This heterogeneous mixture was then evacuated and purged with nitrogen three times prior to introduction of [1,1'-bis-(diphenylphosphino)ferrocene]dichloro-palladium(II), complex with DCM (1:1) (0.426 g, 0.583 mmol). The heterogeneous mixture was then evacuated and purged with nitrogen twice before the septum was replaced with a teflon screw-top cap. This sealed vessel then heated to 90° C. for 1.5 hours. After cooling to ambient temperature potassium carbonate (3.22 g, 23.3 mmol), water (3 mL), compound of Reference Example V (3.74 g, 12.8 mmol) and additional palladium catalyst (0.426 g, 0.583 mmol) were added and the reaction was sealed again. After heating to 80° C. for 3 hours the reaction was cooled and then quenched with water and EtOAc. This aqueous layer was extracted once with EtOAc. The combined organic layers were washed with additional water and then brine prior to drying over sodium sulfate. Filtration and solvent removal provided material which was subjected to silica gel chromatography eluting with 10-35% EtOAc in hexanes. Collection of product containing fractions and removal of solvent yielded 3.62 grams of tert-butyl ((1R)-1-{5-[5-chloro-3-fluoro-2-(5-methyl-1,2,4-oxadiazol-3-yl)phenyl]-3-fluoropyridin-2-yl}ethyl)carbamate.

The above Boc-protected material was dissolved in 100 mL of MeOH and then cooled to 0° C. Anhydrous HCl gas was then bubbled through the solution for 3 minutes. After allowing this reaction mixture to stand at 0° C. for 30 minutes solvent was removed. Additional MeOH was added and then removed under vacuum, followed by addition and removal of DCM (twice) to provide 3.10 g of the amine hydrochloride as a foaming solid.

To the above amine hydrochloride (4.54 g, 11.7 mmol) in a 200 mL round-bottom flask was added anhydrous DCM (31 mL), (2R)-3,3,3-trifluoro-2-hydroxy-2-methylpropanoic acid (2.78 g, 17.6 mmol), HOBt.H$_2$O (0.898 g, 5.86 mmol), triethylamine (2.97 g, 29.3 mmol) and lastly EDCI (3.60 g, 18.8 mmol). This reaction mixture was allowed to stir at ambient temperature for 16 hours. After the reaction was judged complete by LC/MS analysis, the reaction mixture (without work-up or solvent removal) was subjected to silica gel chromatography eluting with 20-60% EtOAc in hexanes. Collection of product containing fractions and removal of solvent yielded 3.61 grams of the title compound as a foaming solid. Purity was determined by LCMS (ES MS, M+H$^+$ found: 491) and proton NMR (400 MHz, CD$_3$OD: δ 8.208, 8.204, 7.569, 7.564, 7.558, 7.546, 7.541, 7.537, 7.533, 7.518, 7.515, 7.513, 7.510, 5.381, 5.366, 5.363, 5.349, 5.346, 5.331, 2.546, 1.576, 1.468, 1.451).

The following compounds were prepared by following the general procedures provided in Examples 1 and 2. The α-hydroxycarboxylic acid starting materials are either commercially available of may be prepared from commercially available reagents using conventional reactions well known in the art. The biarylmethylamine starting materials may be prepared by the procedures provided in the Reference Examples section and in the general reaction schemes, using reagents that are either commercially available or that may be prepared from commercially available reagents using conventional reactions well known in the art.

TABLE 1

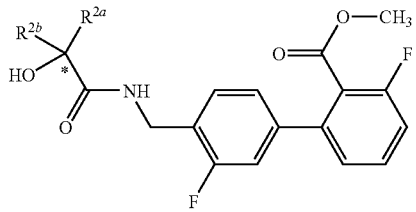

| Ex. | $R^{2a}$ | $R^{2b}$ | * | LRMS (M + H+) |
|---|---|---|---|---|
| 3 | CH₃ | CH₃ | − | 364 |
| 4 | H | H | − | 336 |
| 5 | CH₂CH₃ | CH₂CH₃ | − | 392 |
| 6 | 3-(OCH₃)-Ph | H | ± | 442 |
| 7 | CHCH₃ | CH₃ | ± | 378 |
| 8 | CH(CH₃)₂ | H | ± | 378 |
| 9 | CH₃ | H | S | 350 |
| 10 | Ph | cyclopentyl | ± | 480 |
| 11 | 4-Br—Ph | H | ± | 490 |
| 12 | 4-(CF₃)-Ph | H | ± | 480 |
| 13 | Ph | H | S | 412 |
| 14 | 4-(OCH₃)-Ph | H | ± | 442 |
| 15 | CH₂Ph | H | ± | 426 |
| 16 | cyclohexyl | H | R | 418 |
| 17 | 3-(OH)-4-(OCH₃)-Ph | H | ± | 458 |
| 18 | 3,4-diOH—Ph | H | ± | 444 |
| 19 | CF₃ | CF₃ | − | 472 |
| 20 | CH₂CH(CH₃)₂ | H | ± | 392 |
| 21 | Ph | CH₃ | ± | 426 |
| 22 | (1H-indol-3-yl)methyl | H | ± | 465 |
| 23 | CH₂(CH₂)₄CH₃ | H | ± | 420 |
| 24 | 3,5-diF-Ph | H | ± | 448 |
| 25 | CF₃ | H | ± | 404 |
| 26 | CF₃ | CH₃ | S | 418 |
| 27 | CF₃ | CH₃ | R | 418 |
| 28 | CH₃ | H | R | 350 |
| 29 | (CH₂)₃CH₃ | H | ± | 392 |
| 30 | cyclohexyl | H | S | 418 |
| 31 | CH₂CH(CH₃)₂ | H | S | 392 |
| 32 | CH(CH₃)₂ | H | R | 378 |
| 33 | CH(CH₃)₂ | H | S | 378 |
| 34 | CH(CH₃)CH₂CH₃ | H | S | 392 |
| 35 | C(CH₃)₃ | H | S | 392 |
| 36 | CF₃ | H | S | 404 |
| 37 | CH₂CH₂SCH₃ | H | ± | 410 |
| 38 | CH₂CH(CH₃)₂l | H | R | 392 |
| 39 | (pyridin-3-yl)methyl | H | ± | 427 |
| 40 | OH | CF₃ | − | 420 |
| 41 | CF₂CF₃ | CH₃ | − | 468 |
| 42 | CF₂H | CH₃ | ± | 400 |

TABLE 2

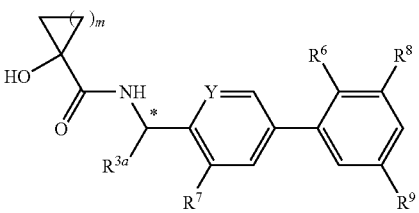

| Ex. | m | $R^{3a}$ | Y | * | $R^6$ | $R^7$ | $R^8$ | $R^9$ | LRMS (M + H+) |
|---|---|---|---|---|---|---|---|---|---|
| 43 | 1 | H | CH | — | CO₂CH₃ | F | F | H | 362 |
| 44 | 2 | H | CH | — | CO₂CH₃ | F | F | H | 376 |
| 45 | 1 | CH₃ | N | R | CO₂CH₃ | F | Cl | Cl | 427 |

TABLE 2-continued

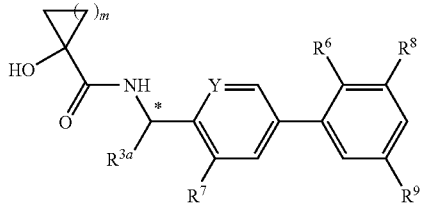

| Ex. | m | $R^{3a}$ | Y | * | $R^6$ | $R^7$ | $R^8$ | $R^9$ | LRMS (M + H+) |
|---|---|---|---|---|---|---|---|---|---|
| 46 | 5 | H | CH | — | CO₂CH₃ | F | F | H | 418 |
| 47 | 1 | CH₃ | N | R | OCH₂CH₃ | F | Cl | Cl | 413 |
| 48 | 1 | CH₃ | CH | R | CO₂CH₃ | F | Cl | H | 392 |
| 49 | 1 | CH₃ | CH | R | CO₂CH₃ | H | F | H | 358 |
| 50 | 1 | CH₃ | CH | S | CO₂CH₃ | F | F | H | 376 |
| 51 | 1 | CH₃ | N | R | OCH₂CHF₂ | F | Cl | Cl | 449 |
| 52 | 1 | CH₃ | CH | R | CO₂CH₃ | Cl | Cl | H | 408 |
| 53 | 1 | CH₃ | CH | R | OCH₂CHF₂ | F | Cl | Cl | 448 |
| 54 | 1 | CH₃ | CH | R | 2-CH₃-2H-tetrazol-5-yl | F | F | H | 400 |
| 55 | 1 | CH₃ | CH | R | CO₂CH₃ | F | Cl | Cl | 426 |
| 56 | 2 | CH₃ | N | R | CO₂CH₃ | F | Cl | Cl | 441 |
| 57 | 1 | CH₃ | N | R | 2-CH₃-2H-tetrazol-5-yl | F | F | H | 401 |

TABLE 3

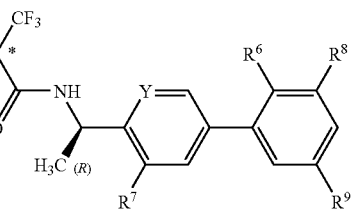

| Example | Y | * | $R^6$ | $R^7$ | $R^8$ | $R^9$ | LRMS (M + H+) |
|---|---|---|---|---|---|---|---|
| 58 | CH | R | CO₂CH₃ | F | Cl | H | 448 |
| 59 | N | R | CO₂CH₃ | F | F | Cl | 467 |
| 60 | N | R | 2-CH₃-2H-tetrazol-5-yl | F | F | H | 457 |
| 61 | N | R | CO₂CH₂CH₃ | F | F | Cl | 481 |
| 62 | N | R | CO₂CH₃ | F | Cl | Cl | 483 |
| 63 | N | R | OCH₂CHF₂ | F | Cl | Cl | 505 |
| 64 | N | R | OCH₂CH₃ | F | Cl | Cl | 469 |
| 65 | CH | R | 2-CH₃-2H-tetrazol-5-yl | F | F | H | 456 |
| 66 | CH | ± | Ph | F | H | H | 432 |
| 67 | CH | R | CO₂CH₃ | F | Cl | Cl | 482 |
| 68 | N | R | CN | F | Cl | Cl | 450 |
| 70 | CH | R | OCH₂CF₃ | F | F | Cl | 504 |
| 71 | CH | R | 3-CH₃-1,2,4-oxadiazole | F | H | Cl | 470 |
| 72 | N | R | OCH₂CF₃ | F | F | Cl | 505 |
| 73 | CH | R | OCH₂CHF₂ | F | Cl | Cl | 504 |
| 74 | CH | R | 2-CH₃-2H-tetrazol-5-yl | F | H | F | 456 |
| 75 | CH | R | CF₃ | F | H | H | 424 |
| 76 | CH | R | 5-CH₃-1,2,4-oxadiazole | F | H | F | 456 |
| 77 | N | R | OCH₂CF₃ | Cl | Cl | Cl | 539 |
| 78 | N | R | 2-CH₃-2H-tetrazol-5-yl | Cl | F | H | 471 |
| 79 | N | R | OCH(CH₃)₂ | F | Cl | Cl | 483 |
| 80 | N | R | 2-CH₃-2H-tetrazol-5-yl | F | Cl | Cl | 507 |
| 81 | CH | R | 3-CH₃-1,2,4-oxadiazole | F | F | H | 456 |
| 82 | CH | R | 2-CH₃-2H-tetrazol-5-yl | F | Cl | Cl | 506 |
| 83 | CH | R | OCH₂CF₃ | F | Cl | Cl | 522 |
| 84 | CH | R | OCH(CH₃)₂ | F | Cl | Cl | 482 |
| 85 | CH | R | CO₂CH₃ | F | F | H | 432 |
| 86 | N | R | CONH₂ | F | Cl | Cl | 468 |
| 87 | N | R | SCH₂CH₃ | F | Cl | H | 449 |
| 88 | N | R | OCH₂CF₃ | F | Cl | Cl | 523 |
| 89 | N | R | 5-CH₃-1,2,4-oxadiazole | F | Cl | Cl | 507 |

TABLE 3-continued

Structure: HO, CF₃, H₃C, *, NH, Y, R⁶, R⁸, R⁷, R⁹ attached as shown; H₃C(R) chiral center.

| Example | Y | * | R⁶ | R⁷ | R⁸ | R⁹ | LRMS (M + H⁺) |
|---|---|---|---|---|---|---|---|
| 90 | N | R | CO₂CH₃ | Cl | F | H | 447 |
| 91 | CH | R | 2-CH₃-2H-tetrazol-5-yl | F | Cl | H | 470 |
| 92 | CH | R | OCH(CH₂CH₃)₂ | F | Cl | Cl | 510 |
| 93 | CH | R | OCH₂CH₂CH₃ | F | Cl | Cl | 482 |
| 94 | CH | R | OCH₂CHF₂ | F | F | F | 472 |
| 95 | CH | R | CO₂CH₂CH₃ | F | Cl | H | 460 |
| 96 | N | R | 2-CH₃-2H-tetrazol-5-yl | Cl | Cl | H | 489 |
| 97 | N | R | OCH₂CHF₂ | F | F | Cl | 487 |
| 98 | N | R | CO₂CH₃ | Cl | Cl | Cl | 499 |
| 99 | N | R | OCH₂CH(CH₃)₂ | F | Cl | Cl | 497 |
| 100 | N | R | CO₂CH₂CH₃ | F | Cl | H | 461 |
| 101 | N | R | CO₂CH₂CH₃ | F | Cl | Cl | 497 |
| 102 | N | R | CO₂CH₃ | F | Cl | H | 447 |
| 103 | N | R | 2-CH₃-2H-tetrazol-5-yl | F | Cl | H | 471 |
| 104 | N | R | S(O)CH₂CH₃ | F | Cl | H | 465 |
| 105 | N | R | CO₂CH₂CH₃ | Cl | Cl | H | 479 |
| 106 | CH | R | CO₂CH₃ | H | H | H | 414 |
| 107 | N | R | 5-CH₃-1,2,4-oxadiazole | F | F | H | 457 |
| 108 | CH | R | CO₂CH₂CH₃ | F | Cl | Cl | 496 |
| 109 | N | R | 2-CH₃-2H-tetrazol-5-yl | Cl | Cl | Cl | 521 |
| 110 | N | R | 5-CH₃-1,2,4-oxadiazole | Cl | Cl | Cl | 521 |
| 111 | N | R | 2-CH₃-2H-tetrazol-5-yl | F | F | Cl | 489 |
| 112 | N | R | 3-CH₃-1,2,4-oxadiazole | F | F | H | 457 |
| 113 | N | R | 5-CH₃-1,2,4-oxadiazole | F | Cl | H | 471 |
| 114 | N | R | 3-CH₃-1,2,4-oxadiazole | F | F | Cl | 489 |
| 115 | CH | R | 2-CH₃-2H-tetrazol-5-yl | F | F | Cl | 488 |
| 116 | N | R | 3-CH₃-1,2,4-oxadiazole | Cl | F | H | 471 |
| 117 | N | R | 3-CH₃-1,2,4-oxadiazole | Cl | F | Cl | 507 |
| 118 | N | R | 5-CH₃-1,2,4-oxadiazole | Cl | Cl | H | 489 |
| 119 | CH | R | 5-CH₃-1,2,4-oxadiazole | F | F | Cl | 488 |
| 120 | N | R | 5-CH₃-1,2,4-oxadiazole | Cl | F | H | 471 |
| 121 | N | R | 2-CH₃-2H-tetrazol-5-yl | Cl | F | Cl | 507 |
| 122 | CH | R | CO₂CH₃ | Cl | Cl | H | 464 |
| 123 | N | R | 3-CH₃-1,2,4-oxadiazole | F | Cl | H | 471 |
| 124 | N | R | 5-CH₃-1,2,4-oxadiazole | F | Cl | F | 489 |
| 125 | N | R | 2-CH₃-2H-tetrazol-5-yl | F | Cl | F | 489 |
| 126 | N | R | CO₂CH₂CH₃ | Cl | Cl | Cl | 511 |
| 127 | N | R | 5-CH₃-1,2,4-oxadiazole | Cl | F | Cl | 507 |
| 128 | N | R | 3-CH₃-1,2,4-oxadiazole | Cl | Cl | Cl | 507 |
| 129 | CH | R | 5-CH₃-1,2,4-oxadiazole | F | F | Me | 470 |
| 130 | CH | R | 1-CH₃-2H-tetrazol-5-yl | F | F | Cl | 488 |
| 131 | CH | R | 2-CH₃-2H-tetrazol-5-yl | Cl | F | Cl | 506 |
| 132 | N | R | 3-CH₃-1,2,4-oxadiazole | Cl | Cl | Cl | 521 |
| 133 | N | R | 2-CH₃-2H-tetrazol-5-yl | F | F | F | 475 |
| 134 | N | R | CO₂CH₃ | H | Cl | Cl | 465 |
| 135 | CH | R | 2-CH₃-2H-tetrazol-5-yl | F | F | Me | 470 |
| 136 | N | R | 5-CH₃-1,2,4-oxadiazole | Cl | Cl | Me | 503 |
| 137 | N | R | 2-CH₃-2H-tetrazol-5-yl | Cl | Cl | Me | 503 |
| 138 | CH | R | OCH₂CH₂CF₃ | F | Cl | Cl | 536 |
| 139 | CH | R | 5-CH₃-1,2,4-oxadiazole | F | Cl | CF₃ | 538 |
| 140 | CH | R | 5-CH₃-1,2,4-oxadiazole | F | H | H | 438 |
| 141 | CH | R | 2-CH₃-2H-tetrazol-5-yl | F | Cl | CF₃ | 538 |
| 142 | N | R | 5-CH₃-1,2,4-oxadiazole | F | F | F | 475 |
| 143 | N | R | 5-CH₃-1,2,4-oxadiazole | Cl | F | F | 489 |
| 144 | N | R | 2-CH₃-2H-tetrazol-5-yl | Cl | F | F | 489 |
| 145 | N | R | SO₂CH₂CH₃ | F | Cl | H | 481 |
| 146 | N | R | 5-CH(CH₃)₂-1,2,4-oxadiazole | F | Cl | Cl | 534 |
| 147 | CH | R | NH(CH₂CF₃) | F | Cl | Cl | 503 |
| 148 | CH | R | 2-CH₃-2H-tetrazol-5-yl | F | Cl | OCF₃ | 554 |
| 149 | N | R | 3-CH₃-1,2,4-oxadiazole | F | F | F | 489 |
| 150 | N | R | 3-CH₃-1,2,4-oxadiazole | Cl | F | F | 489 |
| 151 | N | R | 3-CH₃-1,2,4-oxadiazole | F | F | F | 475 |
| 152 | N | R | 5-CH₃-1,2,4-oxadiazole | F | F | F | 451 |
| 153 | CH | R | 5-CH₃-1,2,4-oxadiazole | F | Cl | SO₂Me | 548 |
| 154 | CH | R | cyclopropyl | F | Cl | Cl | 464 |
| 155 | CH | R | 5-pyrimidinyl | F | Cl | Cl | 502 |
| 156 | CH | R | 2-CH₃-2H-tetrazol-5-yl | Cl | Cl | CO₂CH₃ | 528 |

TABLE 4

| Example | Y | * | R⁶ | R⁷ | R⁸ | R⁹ | LRMS (M + H⁺) |
|---|---|---|---|---|---|---|---|
| 157 | CH | R | CONHCH₃ | F | F | H | 417 |
| 158 | N | R | CO₂CH₃ | Cl | F | H | 433 |
| 159 | CH | R | 2-CH₃-2H-tetrazol-5-yl | Cl | F | Cl | 492 |
| 160 | N | R | 2-CH₃-2H-tetrazol-5-yl | F | Cl | Cl | 493 |
| 161 | N | R | 2-CH₃-2H-tetrazol-5-yl | F | F | Cl | 475 |
| 162 | N | R | 2-CH₃-2H-tetrazol-5-yl | Cl | F | Cl | 493 |
| 163 | CH | R | 5-CH₃-1,2,4-oxadiazole | Cl | F | Cl | 492 |
| 164 | N | R | 5-CH₃-1,2,4-oxadiazole | Cl | F | Cl | 493 |
| 165 | N | R | 2-CH₃-2H-tetrazol-5-yl | Cl | Cl | Cl | 507 |
| 166 | N | R | 3-CH₃-1,2,4-oxadiazole | Cl | F | Cl | 493 |
| 167 | N | R | 2-CH₃-2H-tetrazol-5-yl | Cl | F | H | 457 |
| 168 | N | R | 2-CH₃-2H-tetrazol-5-yl | F | F | F | 461 |
| 169 | N | R | 5-CH₃-1,2,4-oxadiazole | F | F | Cl | 475 |
| 170 | N | R | 2-CH₃-2H-tetrazol-5-yl | F | F | H | 443 |
| 171 | CH | R | CO₂CH₃ | Cl | Cl | Cl | 482 |
| 172 | N | R | 2-CH₃-2H-tetrazol-5-yl | Cl | F | F | 475 |
| 173 | N | R | 2-CH₃-2H-tetrazol-5-yl | Cl | Cl | H | 475 |
| 174 | N | R | 3-CH₃-1,2,4-oxadiazole | Cl | Cl | Cl | 507 |
| 175 | N | R | 5-CH₃-1,2,4-oxadiazole | Cl | F | F | 475 |
| 176 | N | R | 3-CH₃-1,2,4-oxadiazole | Cl | F | F | 475 |
| 177 | N | R | 2-CH₃-2H-tetrazol-5-yl | Cl | Cl | F | 493 |
| 178 | N | R | 3-CH₃-1,2,4-oxadiazole | Cl | Cl | F | 493 |
| 179 | N | R | CO₂CH₃ | Cl | F | Cl | 468 |
| 180 | N | R | 5-CH₃-1,2,4-oxadiazole | Cl | Cl | Cl | 507 |
| 181 | N | R | 5-CH₃-1,2,4-oxadiazole | F | Cl | Cl | 493 |
| 182 | N | R | 3-CH₃-1,2,4-oxadiazole | Cl | Cl | H | 475 |
| 183 | N | R | 5-CH₃-1,2,4-oxadiazole | Cl | Cl | F | 493 |
| 184 | N | R | 3-CH₃-1,2,4-oxadiazole | F | F | Cl | 476 |

What is claimed is:

1. A compound of formula (I) or a pharmaceutically acceptable salt thereof

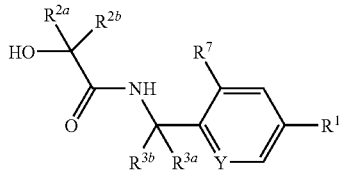

wherein
Y is N;
$R^1$ is

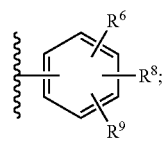

$R^{2a}$ is selected from (1) a group selected from $R^a$, (2) $(CH_2)_n NR^b C(O)R^a$, (3) $(CH_2)_n NR^b SO_2 R^d$, (4) $(CH_2)_n NR^b CO_2 R^a$, (5) $(CH_2)_k CO_2 R^a$, and (6) $(CH_2)_k C(O)NR^b R^c$, $R^{2b}$ is OH or a group selected from $R^{2a}$; or $R^{2a}$ and $R^{2b}$ together with the carbon atom to which they are attached form a 3- to 7-membered carbocyclic ring optionally substituted with 1 to 4 groups independently selected from halogen, $OR^a$, $C_{1-4}$ alkyl and $C_{1-4}$ haloalkyl;

$R^{3a}$ and $R^{3b}$ are independently selected from hydrogen, $C_{1-4}$ alkyl, and $C_{1-4}$ haloalkyl;

$R^6$ is optionally substituted 1,2,4-oxadiazolyl, and wherein said substituent is 1 to 3 groups independently selected from $C_{1-4}$ alkyl optionally substituted with 1 to 5 halogen atoms, $OR^a$ or $OC(O)R^a$;

$R^7$ is selected from hydrogen and halogen;

$R^8$ and $R^9$ are independently selected from (1) hydrogen, (2) $C_{1-8}$ alkyl optionally substituted with 1-5 groups independently selected from halogen, nitro, cyano, $COR^a$, $CO_2R^a$, $C(O)NR^b R^c$, $OR^a$, $OC(O)R^a$, $SR^a$, $SO_2R^d$, $S(O)R^d$, $NR^b R^c$, $NR^b C(O)R^a$, $NR^b SO_2 R^d$, and $NR^b CO_2 R^a$, (3) $C_{3-8}$ cycloalkyl, (4) $C_{2-8}$ alkenyl optionally substituted with $CO_2R^a$, (5) halogen, (6) cyano, (7) nitro, (8) $NR^b R^c$, (9) $NR^b C(O)R^a$, (10) $NR^b CO_2 R^a$, (11) $NR^b C(O)NR^b R^c$, (12) $NR^b C(O)NR^b CO_2 R^a$, (13) $NR^b SO_2 R^d$, (14) $CO_2 R^a$, (15) $COR^a$, (16) $C(O)NR^b R^c$, (17) $C(O)NHOR^a$, (18) $C(=NOR^a)R^a$, (19) $C(=NOR^a)NR^b R^c$, (20) $OR^a$, (21) $OC(O)R^a$, (22) $S(O)_v R^d$, (23) $SO_2 NR^b R^c$, and (24) phenyl optionally substituted with 1 to 3 groups independently selected from halogen, nitro, cyano, $OR^a$, $SR^a$, $C_{1-4}$ alkyl and $C_{1-4}$ haloalkyl, and (25) $OSO_2 R^d$;

$R^a$ is selected from (1) hydrogen, (2) $C_{1-7}$ alkyl optionally substituted with 1 to 5 halogen atoms, OH, SH, O—$C_{1-4}$ alkyl, or S—$C_{1-4}$alkyl, (3) $(CH_2)_k$-phenyl optionally substituted with 1 to 3 groups independently selected from halogen, cyano, nitro, OH, $C_{1-4}$ alkyloxy, $C_{3-6}$ cycloalkyl, $C_{1-4}$ alkyl and $C_{1-4}$haloalkyl, and (4) $C_{3-6}$ cycloalkyl;

$R^b$ and $R^c$ are independently selected from (1) hydrogen, (2) $C_{1-4}$ alkyl optionally substituted with 1 to 5 groups independently selected from halogen, amino, $CO_2R^a$, $OR^a$, mono-$C_{1-4}$alkylamino, and di-$C_{1-4}$alkylamino, (3) $(CH_2)_k$-phenyl optionally substituted with 1 to 3 groups selected from halogen, cyano, nitro, $OR^a$, $CO_2R^a$, $C_{3-6}$ cycloalkyl, $C_{1-4}$ alkyl and $C_{1-4}$haloalkyl, and (4) $C_{3-6}$ cycloalkyl;

$R^d$ is selected from (1) $C_{1-4}$ alkyl, (2) $C_{1-4}$haloalkyl, (3) $C_{1-4}$ alkyloxy, and (4) $(CH_2)_k$-phenyl optionally substituted with 1 to 3 groups selected from halogen, cyano, nitro, $OR^a$, $CO_2R^a$, $C_{3-6}$ cycloalkyl, $C_{1-4}$ alkyl and $C_{1-4}$haloalkyl;

$R^e$ is selected from hydrogen, $C_{1-4}$ alkyl, $C_{1-4}$ haloalkyl, C(O)H and $C(O)C_{1-4}$alkyl;

n is 1, 2, or 3;
k is 0, 1, 2, 3, or 4; and
v is 0, 1, or 2.

2. A compound of claim 1 wherein $R^{2a}$, $R^{2b}$ and the carbon atom to which they are attached form a 3- to 7-membered carbocyclic ring optionally substituted with 1 to 4 groups independently selected from halogen, $OR^a$, $C_{1-4}$ alkyl and $C_{1-4}$ haloalkyl.

3. A compound of claim 1 wherein $R^8$ is hydrogen or 3-halo, and $R^9$ is hydrogen or 5-halo.

4. A compound of claim 1 having the formula (Ia) or a pharmaceutically acceptable salt thereof:

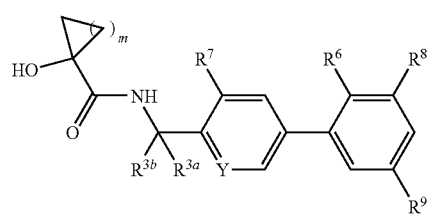

wherein m is 1 to 5; Y is N; one of $R^{3a}$ and $R^{3b}$ is hydrogen and the other is hydrogen or methyl; $R^7$ is hydrogen or fluorine; $R^6$ is 1,2,4-oxadiazolyl; and $R^8$ and $R^9$ are independently hydrogen or halogen.

5. A compound of claim 1 having the formula Ib or a pharmaceutically acceptable salt thereof:

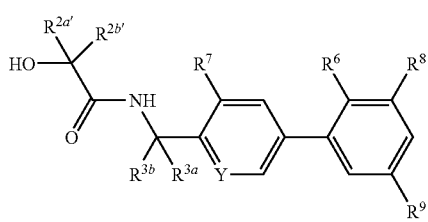

where $R^{3a}$, $R^{3b}$, $R^6$, $R^7$, $R^8$ and $R^9$ are as defined in claim 1, and $R^{2a'}$ and $R^{2b'}$ are independently selected from (1) hydrogen, (2) $C_{1-7}$ alkyl optionally substituted with 1 to 5 halogen atoms, SH, OH, S—$C_{1-4}$alkyl or $OC_{1-4}$alkyl, (3) $(CH_2)_k$-phenyl optionally substituted with 1 to 3 groups independently selected from halogen, cyano, nitro, OH, $C_{1-4}$ alkyloxy, $C_{3-6}$ cycloalkyl, $C_{1-4}$ alkyl and $C_{1-4}$haloalkyl, and (4) $C_{3-6}$ cycloalkyl.

6. A compound of claim 5 wherein $R^{2a'}$ and $R^{2b'}$ are independently $C_{1-7}$alkyl optionally substituted with 1 to 5 halogen atoms.

7. A compound of claim 6 wherein one of $R^{3a}$ and $R^{3b}$ is hydrogen and the other is hydrogen or methyl; $R^7$ is hydrogen, chlorine or fluorine; and $R^8$ and $R^9$ are independently hydrogen or halogen.

8. A compound of claim 1 having the formula Ic or a pharmaceutically acceptable salt thereof:

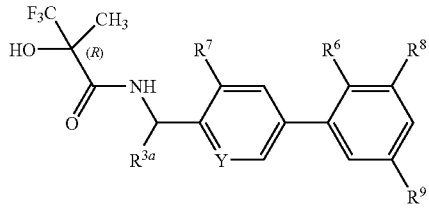

Ic wherein Y is N; $R^7$ is H, chlorine or fluorine; $R^{3a}$ is H or methyl; $R^6$ is 1,2,4-isoxazolyl optionally substituted with a $C_{1-4}$alkyl group; and $R^8$ and $R^9$ are independently hydrogen or halogen.

9. A pharmaceutical composition comprising a therapeutically effective amount of a compound of claim 1 and a pharmaceutically acceptable carrier.

10. A compound of claim 1 being (2R)—N-((1R)-1-{5-[5-chloro-3-fluoro-2-(5-methyl-1,2,4-oxadiazol-3-yl)phenyl]-3-fluoropyridin-2-yl}ethyl)-3,3,3-trifluoro-2-hydroxy-2-methylpropanamide or a pharmaceutically acceptable salt thereof.

* * * * *